(12) United States Patent
Wu

(10) Patent No.: US 11,846,588 B2
(45) Date of Patent: Dec. 19, 2023

(54) DETECTION COMPONENT OF THE PHOTOELECTRIC SMOKE DETECTION FIRE ALARM

(71) Applicant: Xuedan Wu, Yuyao (CN)

(72) Inventor: Xuedan Wu, Yuyao (CN)

( * ) Notice: Subject to any disclaimer, the term of this patent is extended or adjusted under 35 U.S.C. 154(b) by 283 days.

(21) Appl. No.: 16/918,800

(22) Filed: Jul. 1, 2020

(65) Prior Publication Data

US 2021/0156798 A1 May 27, 2021

(30) Foreign Application Priority Data

Nov. 27, 2019 (CN) .......................... 201922077922.3

(51) Int. Cl.
*G01N 21/53* (2006.01)
*G01N 33/00* (2006.01)
*G08B 17/107* (2006.01)

(52) U.S. Cl.
CPC ......... *G01N 21/53* (2013.01); *G01N 33/0036* (2013.01); *G08B 17/107* (2013.01); *G01N 2201/0638* (2013.01)

(58) Field of Classification Search
CPC ....................................................... G01N 21/53
See application file for complete search history.

(56) References Cited

U.S. PATENT DOCUMENTS

| 2007/0012349 A1* | 1/2007 | Gaudiana | G06Q 30/00 |
| | | | 136/244 |
| 2010/0328085 A1* | 12/2010 | Bohanon | G08B 29/24 |
| | | | 340/630 |

* cited by examiner

*Primary Examiner* — Travis R Runnings
(74) *Attorney, Agent, or Firm* — Rumit Ranjit Kanakia

(57) ABSTRACT

The present invention relates generally to fire detection and alarm technology, and more particularly, to a detection component, a detection system and a fire alarm applicable for the Photoelectric Smoke Detection Fire Alarm. The scattering mechanism ensures scattering fitting with the receiving tube to make the size and detection accuracy of the fire alarm fulfill requirements, and the circuit detection system and maze structure improve detection accuracy and reduce the interference of external light.

18 Claims, 21 Drawing Sheets

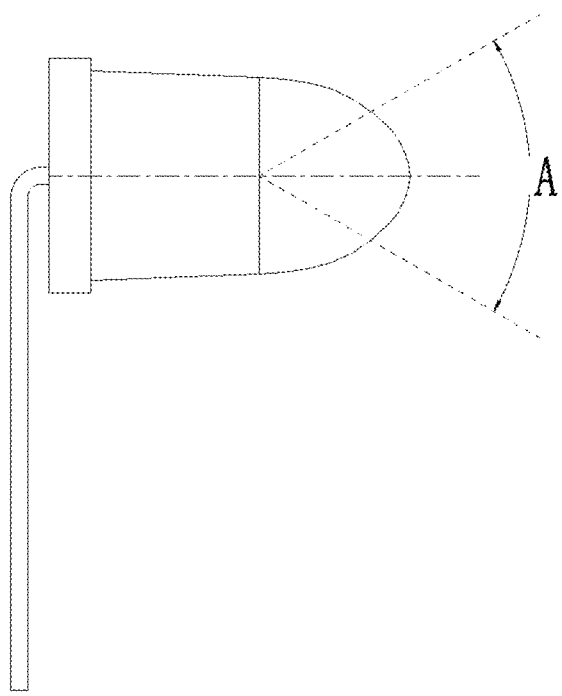
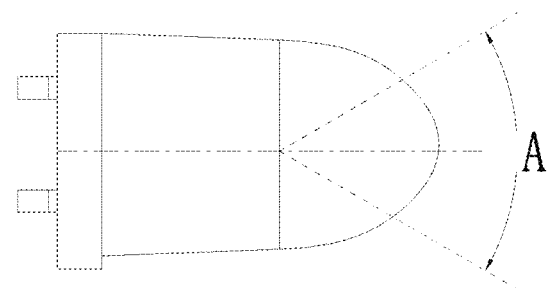
FIG.1a
FIG.1b
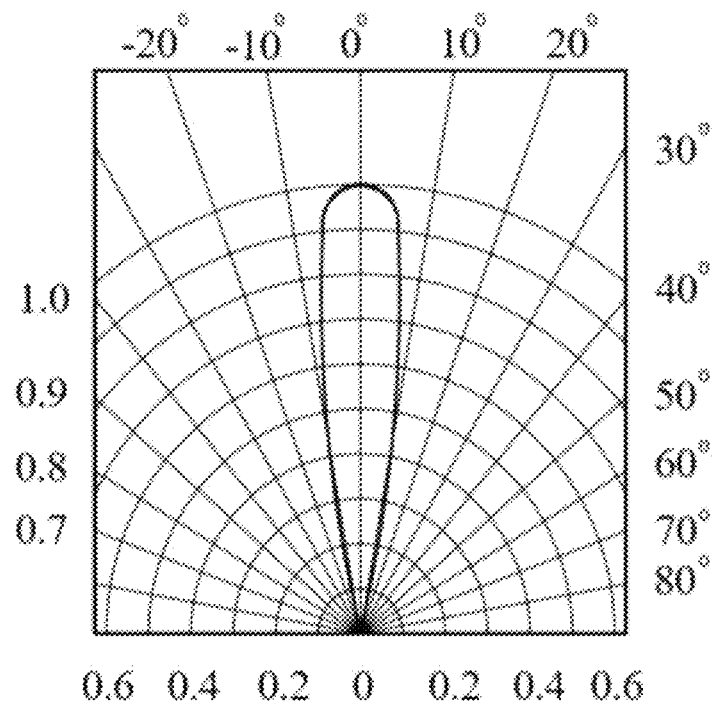
FIG. 1c

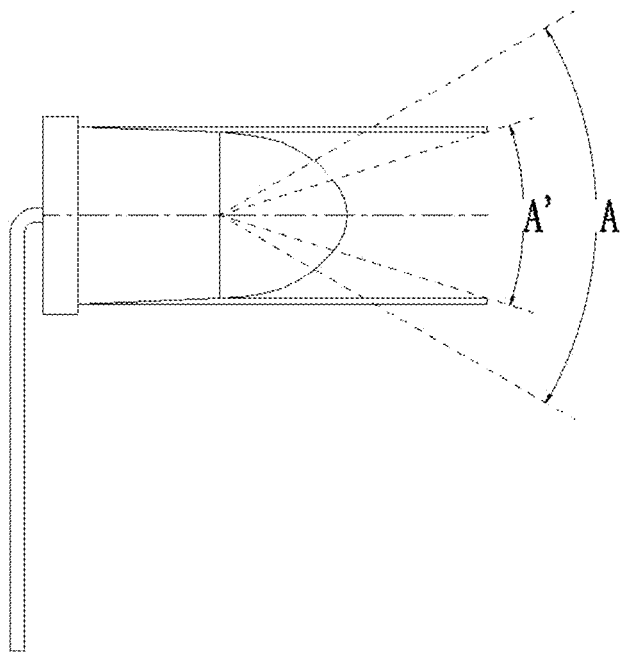
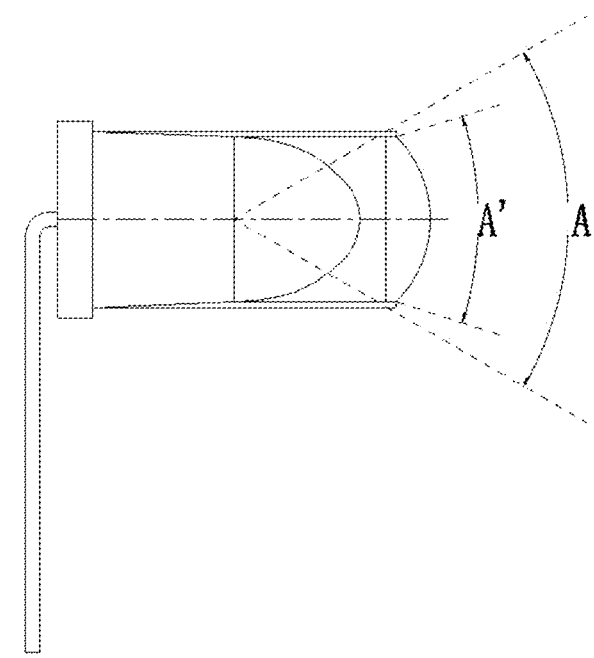
FIG.2a                                    FIG.2b

DETECTION COMPONENT OF THE PHOTOELECTRIC SMOKE DETECTION FIRE ALARM

FIELD OF THE INVENTION

The present invention relates generally to fire detection and alarm technology, and more particularly, to a detection component and a detection system applicable for the photoelectric smoke detector and fire alarm, and a fire alarm having such a detection component.

DESCRIPTION OF THE RELATED ART

Fire refers to a catastrophic combustion that rages out of control in terms of time or space, which is one of the most frequent and common disasters that threaten public security and social development. Once a fire or explosion occurs, heavy casualties and serious economic losses are to be caused. The process of fire is generally divided into five stages: incipient, growth, fully developed, decay and extinguishing. The incipient stage is the best time to extinguish fires given the narrow burning area, small flames, low heat, slow flow of smoke and air, and low speed of burning. Thus, as long as fires in this stage are detected in time, to put out them only requires a small amount of firefighting personnel and equipment. Therefore, for the purpose of extinguishing fire, the incipient and development stage are crucial because the earlier the detection and alarm, the more conducive to fire extinguishing. Hence the fire alarm (also known as the smoke alarm) is of practical significance for preventing fire and reducing loss caused by it.

The type of fire alarm includes smoke alarm (including ionization smoke alarm and photoelectric smoke alarm), thermal alarm (including fixed temperature alarm and rate-of-rise alarm), gas detection alarm, infrared detection alarm, etc. The smoke alarm is the most commonly used fire alarm because many fires begin with billowing smoke and the smoke alarm can sense the smoke and sound the alarm so that fires can be put out before they build up.

Photoelectric smoke alarm, mainly composed of light source, photoelectric element and electronic switch, detects smoke in the initial stage of fires according to the light scattering principle and timely activate fire alarm. Depending on its structural characteristics, photoelectric smoke alarm can be generally divided into the light-shielding type and light-scattering type. As for the light scattering type smoke alarm, the positions of its light-emitting diode and photoelectric element (namely the receiving tube) are not corresponding so that the light cannot shine into the photoelectric element and the circuit remains normal when there is no smoke, but when the smoke enters into the detector in the event of fire, the light can be received by the photoelectric element through reflection or scattering by smoke particles, and the optical signal can be converted into electric signal to send out alarm signal after the electric signal is amplified by the amplifying circuit.

In general, the emitting angle of existing universal emitting tube ranges from 10° to 170°, but the view angle is usually 16°, 18°, 20°, 30° and 40° (view angle referring to 60% angle range of the central light intensity). The receiving angle of receiving tube ranges from 0° to 180°. The size range of existing fire alarms is generally 100-120 mm in diameter and 25-60 cm in height. As shown in FIG. 1a and FIG. 1b, for an emitting tube, its emitting angle remains the same on any cross section passing through the central axis, thereby forming a cone-shaped optical signal emitting range (namely the view angle). Therefore, if, within the existing fire alarm, the universal emitting tube is used as the first emitting tube401 and the second emitting tube402 in the present invention of detection component, then the scattering cooperation between the emitting tube and the receiving tube is difficult to realize, no matter how the relative position and the pitch angle of the emitting tube and the receiving tube 403 change.

And if the size of fire alarm exceeds the current size limit (that is, not considering the size limit on fire alarms) and the existing emitting tube and receiving tube are adopted and their located positions on the bottom plate (400) are configured according to the scattering cooperation method mentioned above, then the thickness of fire alarm is likely to surpass the standard and the accuracy and precision of detection may be reduced. Obviously, this will make the external dimensions of the finished fire alarm significantly exceed the current size design, leading to inconvenience for installation and use.

Therefore, it is necessary to innovate the structure of the existing Photoelectric Smoke Detection Fire Alarm, improve its detection accuracy, and ensure that the external size will not be significantly enlarged.

SUMMARY OF THE INVENTION

The object of the invention is to provide a detection component and a detection system that are highly accurate in detection and easy to manufacture and assembly, as well as a Photoelectric Smoke Detection Fire Alarm equipped with said detection component.

The first part of the invention is to provide a new type of detection component used for the Photoelectric Smoke Detection Fire Alarm which comprises bottom plate. Said bottom plate has a first emitting tube, a second emitting tube and a receiving tube. The first emitting tube and the second emitting tube are fitted to the receiving tube in a scattering manner. The detection component should also comprise scattering mechanism to make the optical signals emitted by the first emitting tube and the second emitting tube not directly received by the receiving tube. The scattering mechanism may include an angle control mechanism such as a light-shielding tube and a refraction lens or a screen to allow the two emitting tubes to fit to the receiving tube in a scattering manner. At least one of the above solutions can realize the application of detection component and ensure detection accuracy under the condition that the size of fire alarm does not change or basically remains unchanged.

The second part of the invention is to provide a detection system for fire detector which comprises a signal modulation module, a photoelectric conversion module and a signal amplification module. The light receiving module is installed at the input end of the photoelectric conversion module and the light emitting module is installed on the signal modulation module. The output end of the photoelectric conversion module is linked with the input end of the signal amplification module and the output end of the signal amplification module is linked with the input end of the signal modulation module. The signal modulation module is used for output modulation signal to modulate the light emitting mode of the light emitting module.

The third part of the invention is to provide a new Photoelectric Smoke Detection Fire Alarm which comprises a detector and an optical maze. The optical maze has a base. One side of the base is a maze portion. And the detector is fitted on this side to form a fire alarm. The detector also uses the above-mentioned detection component for Photoelectric Smoke Detection Fire Alarm as its detection component. This can not only reduce interference of external light but also ensure that the size and accuracy of fire alarms meet the requirements.

The detection component for Photoelectric Smoke Detection Fire Alarm of the present invention, thanks to innovation in its structure, can increase detection accuracy and precision, effectively avoid adverse effects of interference sources, and accurately detect various types of fires.

The detection system of the present invention can modulate the optical signal emitted by the emitting tubes and allow CPU to modulate dynamically via the detection component to adapt to different smoke. For instance, the detection accuracy is significantly increased by dynamically modulating the current waveform according to the smoke concentration or its particle size and selecting the suitable optical signal for detection. When it is used jointly with the detection component of the present invention for Photoelectric Smoke Detection Fire Alarm, it can simultaneously modulate optical signals emitted by the two emitting tubes so as to further increase detection accuracy and reduce false alarm rate. Meanwhile the detection system can also be used independently as its dynamic modulation function also has significant effect on improving the detection accuracy of the conventional Photoelectric Smoke Detection Fire Alarm.

The Photoelectric Smoke Detection Fire Alarm of the present invention comprises said detection component so that its detection accuracy and precision fulfill the requirements. Moreover, the maze structure can further reduce interference from external light in the detector.

BRIEF DESCRIPTION OF THE DRAWINGS

FIGS. 1a and 1b are schematic diagrams of emission parameters of existing emitting tube. More specifically, FIG. 1a and FIG. 1b are schematic diagrams of emission angle as seen from front and top respectively. FIG. 1c is the relation graph of relative gradient, intensity, and angular displacement for emitting tube with a view angle of 18°. The arc curves radiating outward from the emission point 0 are relative intensity and gradient reference lines from 0.1 to 1.0 respectively. The straight lines radiating from the emission point 0 to both sides are angular displacement reference lines from 0° to 90°. The closed solid line area between −10° and 10° is the actual view angle range of the emitting tube.

FIGS. 2a and 2b are schematic diagrams of two emission angle range control structures of the present invention. More specifically, FIG. 2a is a schematic diagram of emission angle range control in case of the light-shielding tube, wherein angle A is the original emission angle range of the emitting tube and angle A' is the emission angle range after control. FIG. 2b is the schematic diagram of emission angle range control in case of the refractive lens, wherein angle A is the original emission angle range of the emitting tube and angle A' is the emission angle range after control.

FIG. 14a is a schematic structural diagram of the first type optical signal modulation module having three current control branches I1, I2 and I3. FIG. 14b is a schematic diagram of the first type optical signal modulation module of which the current control branches are extended to I1 . . . In.

FIG. 15a is a schematic structural diagram of the second type optical signal modulation module having three current control branches I1, I2 and I3. FIG. 15b is a schematic diagram of the second type optical signal modulation module of which the current control branches are extended to I1 . . . In.

FIG. 16a is a schematic structural diagram of the third type optical signal modulation module having three current control branches I1, I2 and I3. FIG. 16b is a schematic diagram of the third type optical signal modulation module of which the current control branches are extended to I1 . . . In.

FIG. 17a is a schematic structural diagram of the fourth type optical signal modulation module having three current control branches I1, I2 and I3. FIG. 17b is a schematic diagram of the fourth type optical signal modulation module of which the current control branches are extended to I1 . . . In.

FIGS. 19a and 19b are schematic structural diagrams of Photoelectric Smoke Detection Fire Alarm according to another embodiment of the present invention, wherein, FIG. 19a is a schematic diagram of an overall structure thereof, and FIG. 19b is a decomposition structural diagram of main components.

FIGS. 20a and 20b are schematic structural diagrams of an upper cover in the embodiment of FIGS. 19a and 19b, wherein, FIG. 20a is a schematic three-dimensional structure diagram thereof, and FIG. 20b is a sectional view thereof.

FIG. 29a, FIG. 29b and FIG. 29c are schematic diagrams of three types of impulsive current, respectively.

DESCRIPTION OF THE PREFERRED EMBODIMENT

Figure 3:
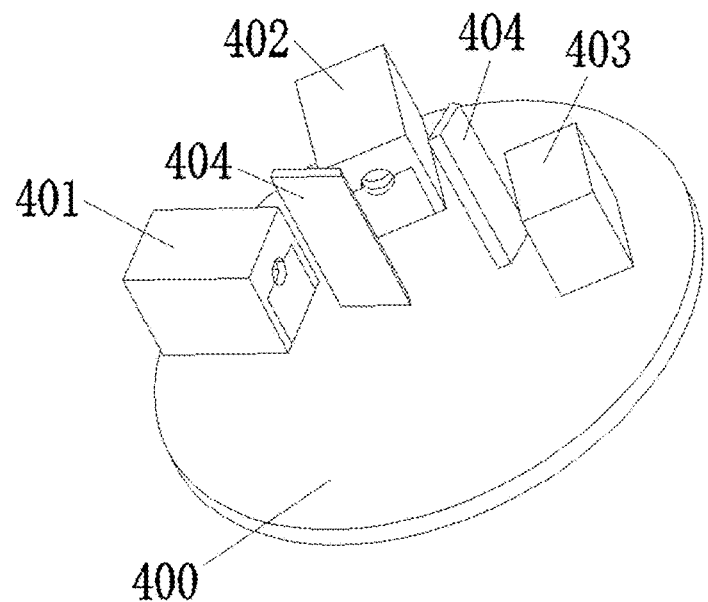
FIG. 3 is a schematic three-dimensional structure diagram of the detection component in embodiment 1 of the present invention.

In order to enable those skilled in the art to better understand the present invention so that the requested protection scope of the present invention can be more clearly defined, some preferred embodiments of the present invention are described in detail hereinafter. It should be noted that the following embodiments are only part of the embodiments of the present invention and the detailed and direct description of relevant structures is only for the convenience of understanding. Therefore, specific features thereof do not surely and directly limit the embodiment scope of the present invention. The regular selection and replacement as well as the reasonable arrangement and reorganization of relevant technical features of the present invention made by those skilled in the art under the guidance of concept in the present invention shall all be regarded as within the requested protection scope of the present invention.

A new type of detection component for Photoelectric Smoke Detection Fire Alarm comprising the bottom plate 400 where a first emitting tube 401, a second emitting tube 402 and a receiving tube 403 are set. The first emitting tube 401 and the second emitting tube 402 are fitted with the receiving tube 403 in a scattering manner on the bottom plate 400; namely optical signals emitted by the first emitting tube 401 and the second emitting tube 402 cannot be received directly by the receiving tube 403 and needs to be scattered or reflected by other media (such as to-be-detected smoke).

In order to solve the technical problem addressed by the present invention, with the size of fire alarm remaining basically unchanged, the component parameters, the structure (also including the relative position), etc. of the detection component are set to meet the above requirements through emission angle range control of the emitting tube, receiving angle range control of the receiving tube, relative position setting of the emitting tube and the receiving tube and partial shielding via obstacles. To be specific, including:

1. Emission angle range control. Customize emitting tube with smaller emission angle range or use parts such as light-shielding tube, refraction lens, etc. to reduce the actual emission angle range of the emitting tube so that the two emitting tubes can cooperate with the receiving tube to achieve scattering even within the current size limit for fire alarms.

For example, as shown in FIG. 2a, a hollow and opaque light-shielding tube is set on the emitting tube to reduce the emission angle range of the emitting tube from the original angle A to angle A'. As can be seen from the figure, the angle range is significantly reduced and controlled by the shape of the shielding tube. As shown in FIG. 2b, a lens is installed at the front end of the emitting tube to reduce the emission angle range of the emitting tube from the original angle A to the angle A'. As can be seen from the figure, the angle range is significantly reduced and controlled by the parameters and setting position of the lens.

The light-shielding tube and the refraction lens are two relatively simple and practical schemes for controlling emission/receiving angle range which can be applied independently or jointly to control the emission angle of existing emitting tube to meet the requirements of detection component. Meanwhile, the specific parameters of said light-shielding tube and lens are not specified herein as they can be set as required.

2. Shielding: namely the bottom plate 400 is fixed with an additional screen 404 which is set between the first emitting tube 401 and/or the second emitting tube 402 and the receiving tube 403 to prevent the optical signals emitted by the first emitting tube or the second emitting tube with a larger emission angle range from being directly received by the receiving tube. In principle, the specific shape and position of the screen 404 are not limited. And all the methods that can block the direct communication between the emitting tube and the receiving tube (that is, preventing optical signals of the emitting tube from being received directly by the receiving tube after straight-line transmitting) are feasible.

For example, as shown in FIG. 3-8, the number of the screen404 may be one, two, or more. And to control the emission angle of the two emitting tubes so as to prevent optical signals from being directly received by the receiving tube 403, the setting position of the screen may be located between the first emitting tube 401 and the second emitting tube 402 and the receiving tube 403 or set in a common area between the three.

The above are the two main methods of scattering coordination. For these two methods, in order to make the central optical axes of the two emitting tubes not coincide, parts can be further set via plane misplacement and three-dimensional misplacement:

First, plane misplacement.

Figure 4:
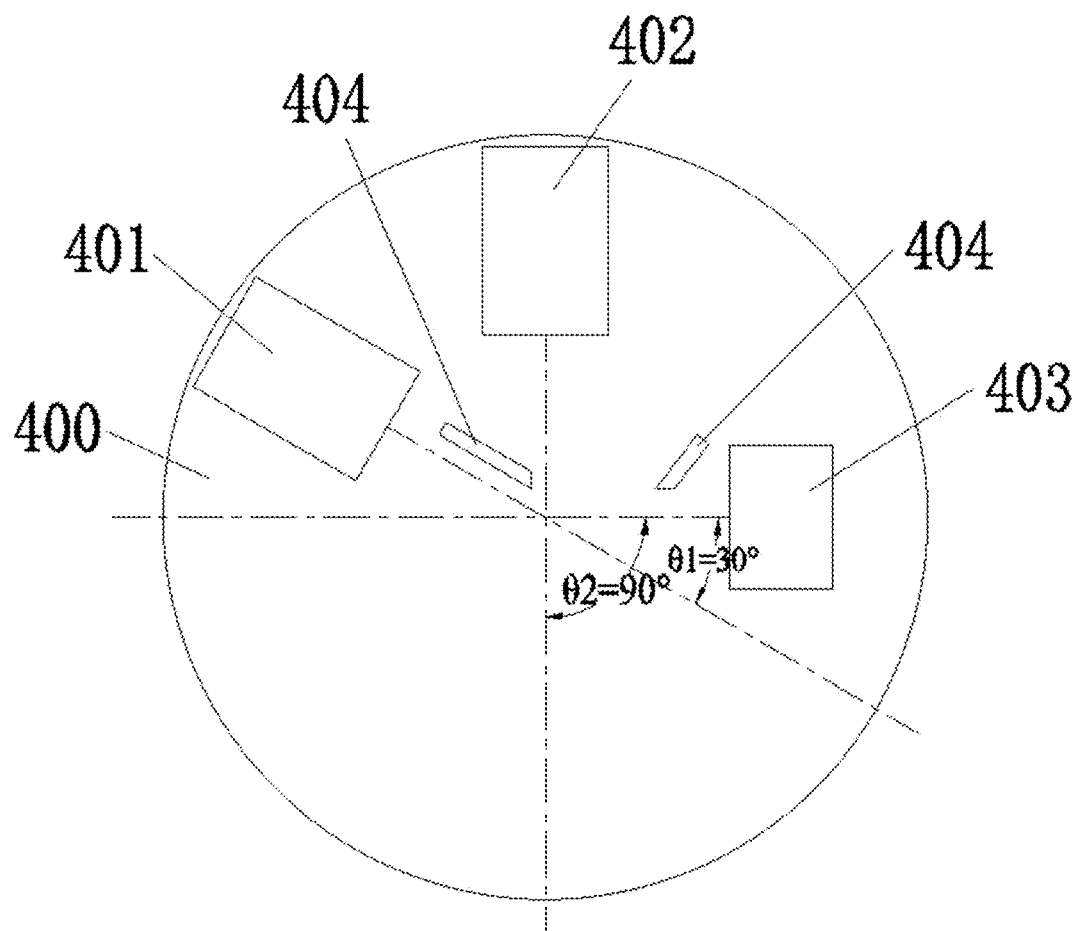
FIG. 4 is a top view of the embodiment in FIG. 3, wherein the centerline is the central axis of the emitting tube/the receiving tube, and θ1 and θ2 are the angular dependence between the first emitting tube and the receiving tube and between the second emitting tube and the receiving tube respectively.

The structural layout is shown in FIG. 3 and FIG. 4. The first emitting tube 401, the second emitting tube 402, and the receiving tube 403 are arranged on the bottom plate 400 on their respective central axes in a coplanar or parallel manner. For instance, their respective central axes are all parallel to the surface or center plane of the bottom plate 400. In short, it is feasible as long as the central axes of the three are coplanar or the planes on which they are located are parallel. In addition, the first emitting tube 401, the second emitting tube 402 and the receiving tube 403 are disposed on the bottom plate 400 in a triangular shape so as to avoid that the first emitting tube 401 and the second emitting tube 402 have the same emission angle.

Also, as shown in FIG. 3 and FIG. 4, the current emitting tube is adopted without controlling its emission angle and two screens 404 are set between the first emitting tube 401 and the second emitting tube 402 and the receiving tube 403 to achieve scattering cooperation between the two emitting tubes and the receiving tube. Surely, without installing the screens 404, it is also feasible to control the emission angle of the two emitting tubes (the specific method being the same as above) and set the relative positions of the emitting tubes and the receiving tube.

Second, three-dimensional misplacement.

Figure 7:
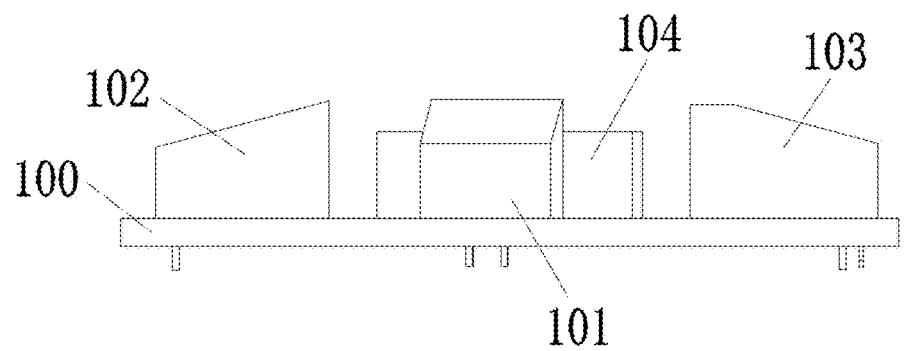
FIG. 7 is a side view of the embodiment in FIG. 6.
Figure 8:
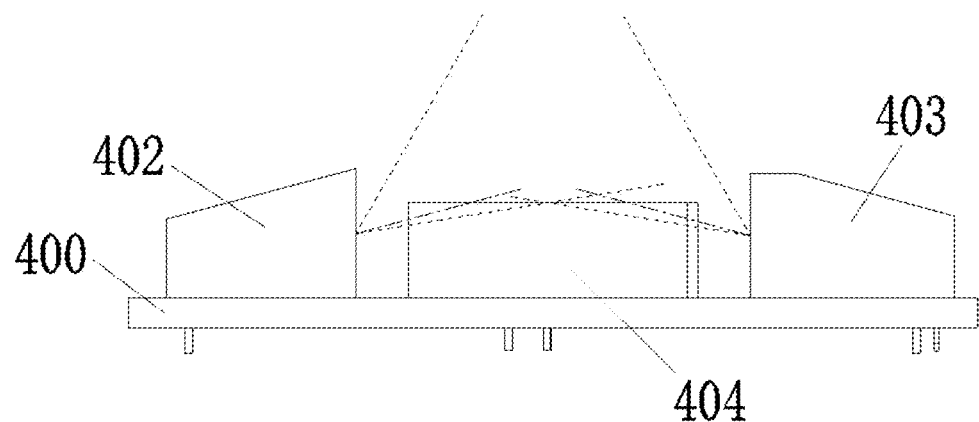
FIG. 8 is a schematic diagram of the actual emission/reception angle range controlled via the screen in the embodiment of FIG. 6.

The structural layout is shown in FIG. 7 and FIG. 8. The first emitting tube 401, the second emitting tube 402, and the receiving tube 403 are disposed on the bottom plate 400 in an up-tilting way on their respective central axes. In principle, the inclination angles of the three are not limited but considering practical application, to make the overall height controllable, the inclination angles of the first emitting tube 401 and the receiving tube 403 can be the same and the inclination angle of the second emitting tube 402 should be smaller than that of the former (namely the inclination angle of the first emitting tube 401 or the receiving tube 403). The first emitting tube 401, the second emitting tube 402 and the receiving tube 403 are set on the bottom plate 400 in a triangular shape so as to avoid that the first emitting tube 401 and the second emitting tube 402 have the same emission angle.

Figure 5:
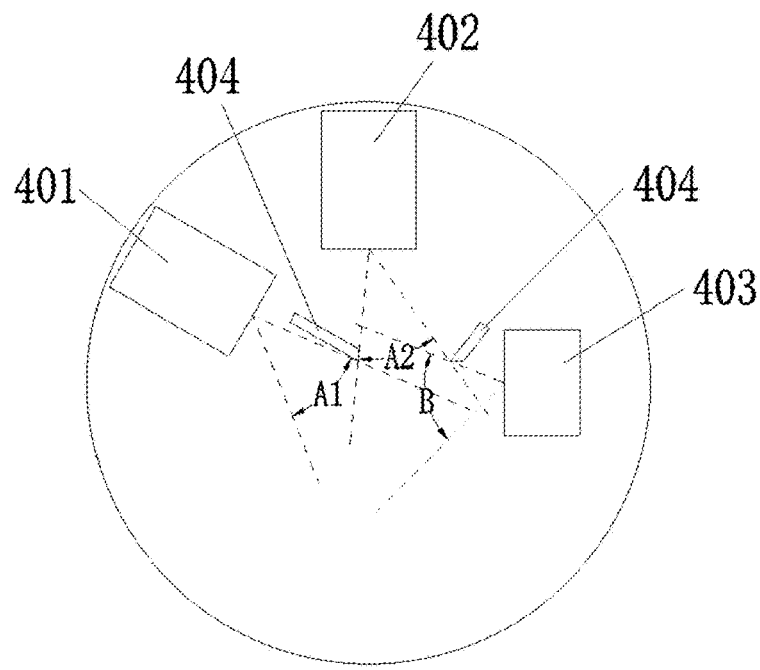
FIG. 5 is a schematic diagram of the actual emission/reception angle range controlled via the screen in the embodiment of FIG. 3.
Figure 6:
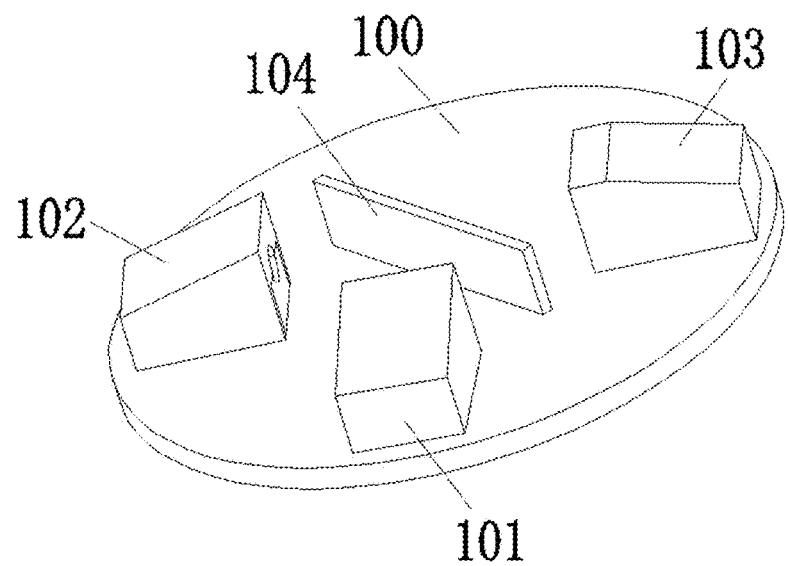
FIG. 6 is a schematic three-dimensional structure diagram of the detection component in embodiment 2 of the present invention.

Also, as shown in FIG. 5 and FIG. 6, the current emitting tube is adopted without controlling its emission angle and a strip-shaped screen404 is set between the first emitting tube 401, the second emitting tube 402 and the receiving tube 403 to achieve scattering cooperation between the two emitting tubes and the receiving tube. Surely, without installing the screens 404, it is also feasible to control the emission angle of the two emitting tubes (the specific method being the same as above) and set the relative positions of the emitting tubes and the receiving tube.

It is worth noting that for this structural layout, light-shielding tube is a better method for angle control. (It can also be understood as a modification of the screen 404.) In addition, for the above two structural layouts, scattering fitting is mainly achieved by combining the emitting tubes and the screen 404, but this does not mean that the emission angle control cannot be applied jointly.

Embodiment 1

As shown in FIG. 3 and FIG. 4, a new type of detection component for Photoelectric Smoke Detection Fire Alarm comprising a bottom plate 400 which is in the shape of a flat cylindrical. A first emitting tube 401, a second emitting tube 402 and receiving tube 403 are fixed on the surface of the bottom plate 400 is fixed. And the first emitting tube 401 and the second emitting tube 402 are fitted with the receiving tube 403 on the bottom plate 400 to achieve scattering; namely optical signals emitted by the first emitting tube401 and the second emitting tube 402 cannot be received directly by the receiving tube 403 but need to be scattered or reflected by other media (such as smoke to be detected) before being received by the receiving tube 403.

To achieve scattering fitting between the two emitting tubes and the receiving tube, the bottom plate 400 is equipped with two screens 404. One is disposed at one side of the anterior part of the first emitting tube 401 to shelter the optical axis on the side of the first emitting tube 401 from being directly received by the receiving tube403, the other screen 404 is disposed at one side of the head of the second emitting tube 402 to shelter the optical axis on the side of the second emitting tube from being directly received by the receiving tube 403. In other words, the function of the two screens 404 is to prevent optical signals emitted by the first emitting tube 401 and the second emitting tube 402 from being directly received by the receiving tube 403. And relevant structural modifications that fulfill this requirement are all feasible. Therefore, no limitations are placed herein.

The central optical axes of the first emitting tube 401, the second emitting tube 402 and the receiving tube 403 are located on the same plane and are parallel to the surface of the bottom plate 400. The screen 404 has a certain height so that its upper edge is higher than the effective emitting height of the first emitting tube 401 and the second emitting tube 402: namely the scattering fitting between the first emitting tube 401, the second emitting tube 402 and the receiving tube 403 is realized in a plane (needless to say, a certain range above and below the plane is also included) rather than over the top of the screen 404 three-dimensionally.

The range of emitting and receiving angles in this embodiment is shown in FIG. 5, in which three angles are marked. And A1, A2, and B are the actual emitting/receiving angle ranges of the first emitting tube 401, the second emitting tube 402, and the receiving tube 403, respectively. It is apparent that the emitting tubes and the receiving tube do not fit directly (that is to say, the two can only fit in a scattering manner).

Embodiment 2

As shown in FIG. 6 and FIG. 7, a new type of detection component for Photoelectric Smoke Detection Fire Alarm comprising a bottom plate 400 which is in the shape of a flat cylindrical. On the surface of the bottom plate 400 is fixed a first emitting tube 401, a second emitting tube 402 and a receiving tube 403. And the first emitting tube 401 and the second emitting tube 402 are fitted with the receiving tube 403 on the bottom plate 400 to achieve scattering; namely optical signals emitted by the first emitting tube401 and the second emitting tube 402 cannot be received directly by the receiving tube 403 but need to be scattered or reflected by other media (such as smoke to be detected) before being received by the receiving tube 403. The first emitting tube 401, the second emitting tube 402 and the receiving tube 403 are set on the bottom plate 400 in a triangular shape. The included angle between the first emitting tube 401 and the receiving tube 403 is 900 and the included angle between the second emitting tube402 and the receiving tube 403 is 180°.

In order to realize the scattering fitting between the two emitting tubes and the receiving tube, a screen 404 is provided on the bottom plate 400. The screen 404 is in the shape of a strip and is arranged in the common area between the first emitting tube 401, the second emitting tube 402 and the receiving tube 403. Moreover, the first emitting tube 401, the second emitting tube 402, and the receiving tube 403 are all disposed on the bottom plate 400 in an inclined and pitching manner as against to the surface of bottom plate 400. The included angle between the central axis of the first emitting tube 401 and the plane of the bottom plate 400 can be the same as the included angle between the central axis of the receiving tube 403 and the plane of the bottom plate 400. The included angle between the central axis of the second emitting tube 402 and the plane of the bottom plate 400 can be smaller than the former, namely the included angle between the central axis of the receiving tube 403 and the plane of bottom plate 400). It should be noted that the surface of the bottom plate 400 is used as a reference surface to determine the inclination relation between the first emitting tube 401, the second emitting tube 402 and the receiving tube 403. The reference surface can also be the bottom surface or the center surface of the bottom plate 400 or other uniquely determined virtual reference surface.

In order to achieve the direct path shielding between the emitting tubes and the receiving tube, the screen 404 should have an appropriate height, and considering the shielding between the two emitting tubes at the same time, the screen 404 is tilted horizontally in the horizontal plane. Thus, the optical signals emitted by the first emitting tube 401 and the second emitting tube 402 cannot be directly received by the receiving tube 403, but are scattering fitted in a three-dimensional direction after crossing the top of the screen 404.

It should be noted that in this embodiment, since the included angle between the first emitting tube 401 and the receiving tube 403 is 90°, the screen 404 does not work on it in principle, but when their angle or distance change enables the optical signal emitted by the first emitting tube 401 to be received directly by the receiving tube 403, the screen 404 also needs to block the direct reception accordingly. The height and length of the screen 404 can be set according to requirements. As long as it can achieve the blocking of direct fitting, the specific situation is not limited.

The emitting and receiving angle ranges in this embodiment are as shown in FIG. 8, where two angles marked are actual emitting/receiving angle ranges of the second emitting tube 402 and the receiving tube 403, respectively. It is apparent that in this case the emitting tube is not fitted directly to the receiving tube (that is to say, the two can only fit in a scattering manner).

Embodiment 3

Figure 9:
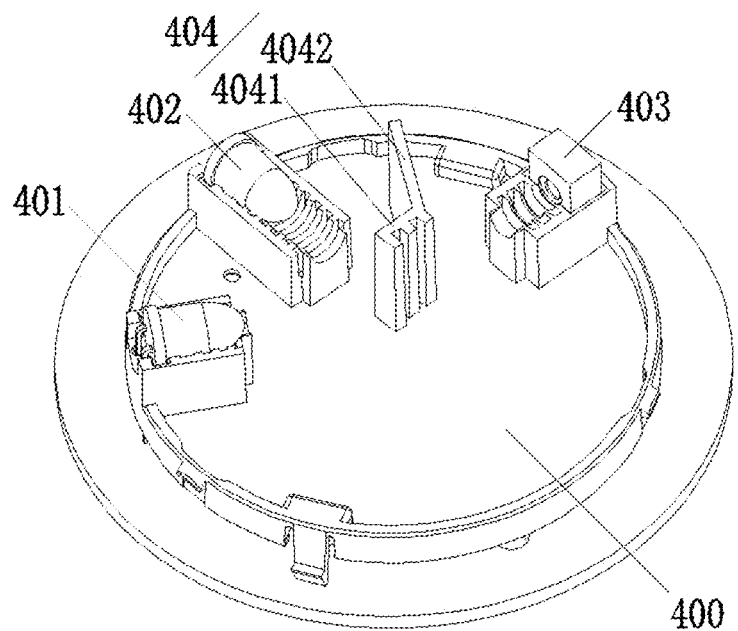
FIG. 9 is a schematic three-dimensional structure diagram of the detection component in embodiment 3 of the present invention.
Figure 10:
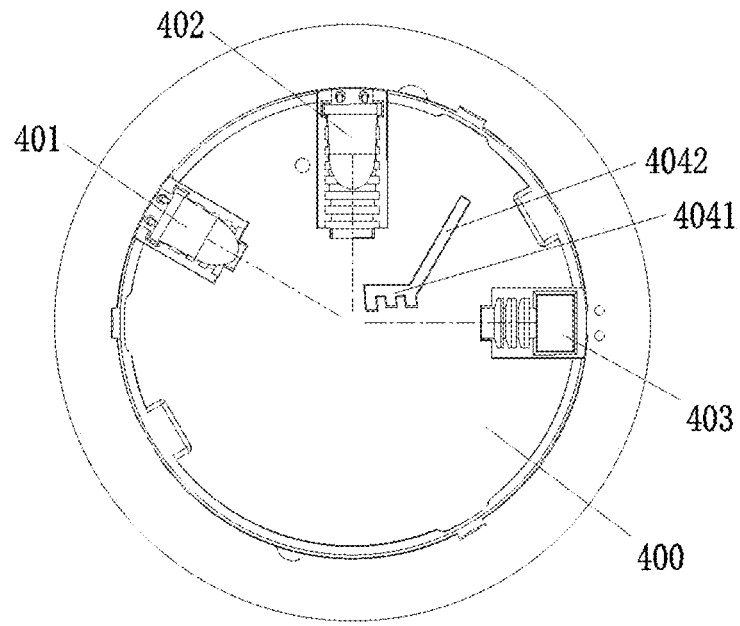
FIG. 10 is a top view of the embodiment in FIG. 9, wherein the centerline is the central axis of emitting tube/the receiving tube.

As shown in FIG. 9 and FIG. 10, a new type of detection component for Photoelectric Smoke Detection Fire Alarm comprising a bottom plate 400 which is in the shape of a flat cylindrical. On the surface of the bottom plate 400 is fixed the first emitting tube 401, the second emitting tube 402 and the receiving tube 403. And the first emitting tube 401 and the second emitting tube 402 are fitted with the receiving tube 403 on the bottom plate 400 to achieve scattering; namely optical signals emitted by the first emitting tube 401 and the second emitting tube 402 cannot be received directly by the receiving tube 403 but need to be scattered or reflected by other media (such as smoke to be detected), then received by the receiving tube 403.

To realize the scattering fitting between the two emitting tubes and the receiving tube, the bottom plate 400 is equipped with a screen 404. The screen 404 comprises the first shielding part 4041 and the second shielding part 4042. The first shielding part 4041 shields a part of the emitting angle of the first emitting tube to shelter its optical signals from being directly received by the receiving tube 403. The first shielding part 4041 and the second shielding part 4042 jointly shield a part of the emitting angle of the second emitting tube 402 to shelter its optical signals from being directly received by the receiving tube 403. Therefore, the first emitting tube 401 and the second emitting tube 402 are both fitted to the receiving tube 403 in a scattering manner.

The central optical axes of the first emitting tube 401, the second emitting tube 402 and the receiving tube 403 are located on the same plane and are parallel to the surface of the bottom plate 400. The screen 404 has a certain height so that its upper edge is higher than the effective emitting height of the first emitting tube 401 and the second emitting tube 402: namely the scattering fitting between the first emitting tube 401, the second emitting tube 402 and the receiving tube 403 is realized in a plane (needless to say, also including a certain range above and below the plane) rather than over the top of the screen 404 three-dimensionally.

Figure 11:
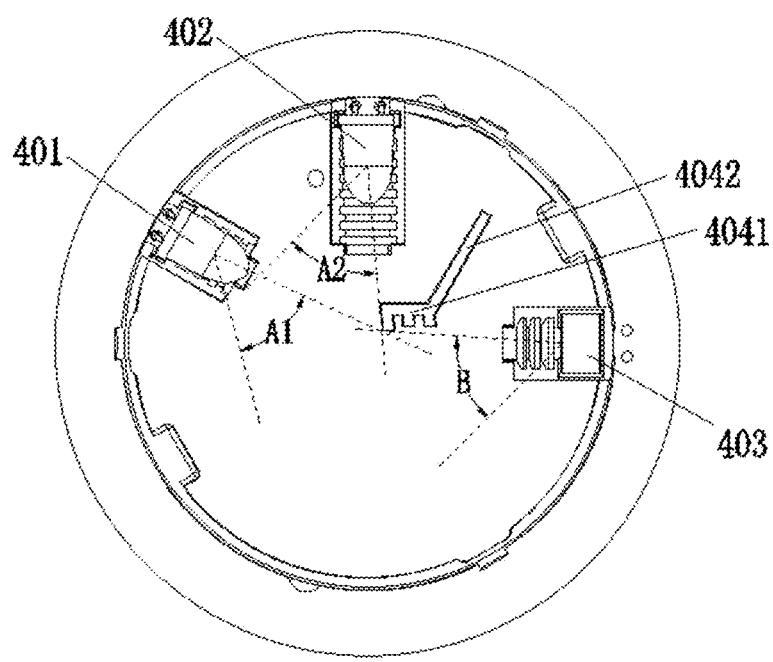
FIG. 11 is the schematic diagram of the actual emission/reception angle range controlled via the screen in the embodiment of FIG. 9.
Figures 12, 13:
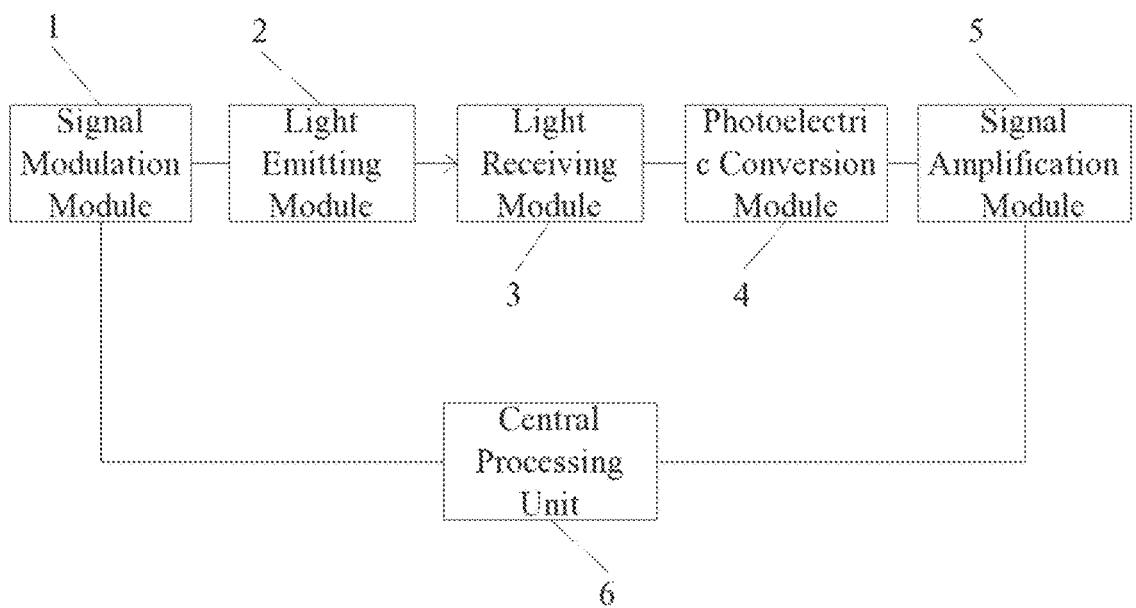
FIG. 12 is a schematic structural diagram of an overall system module in the embodiment.
FIG. 13 is a schematic structural diagram of the central processing unit in the embodiment.
Figure 14A:
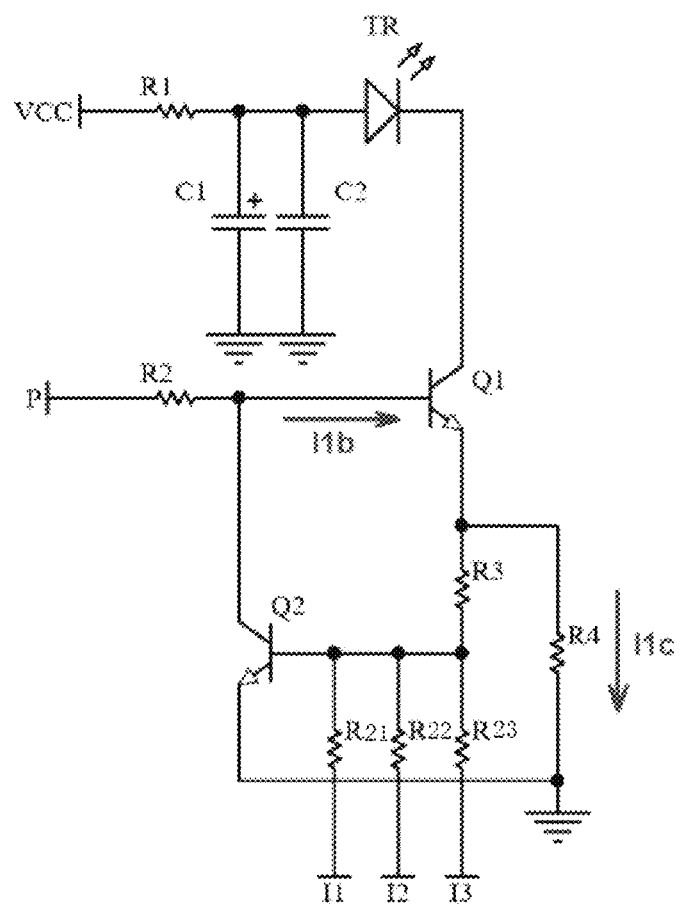
FIGS. 14a and 14b are two optical signal modulation modules of the first type in the embodiment.
Figure 14B:
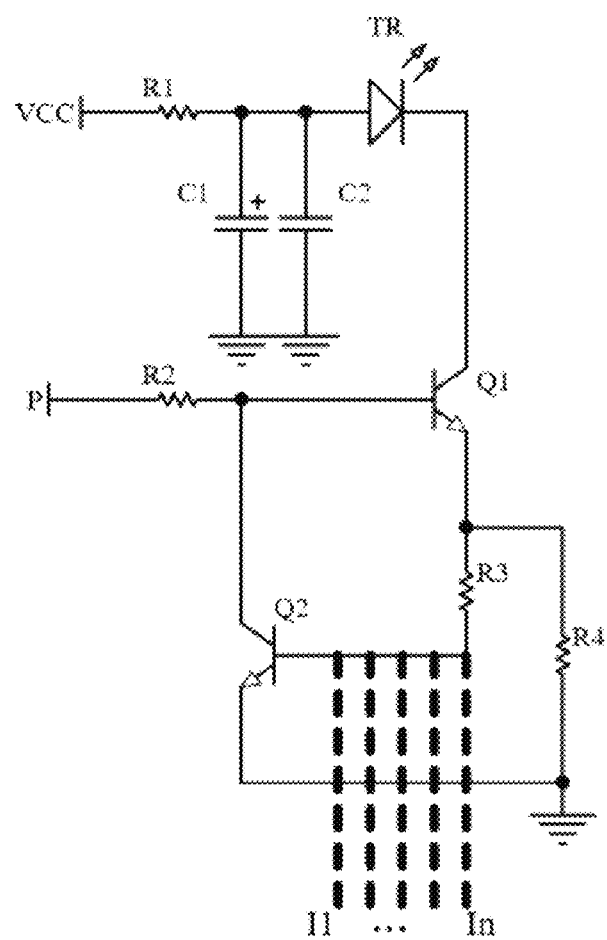
Figure 15A:
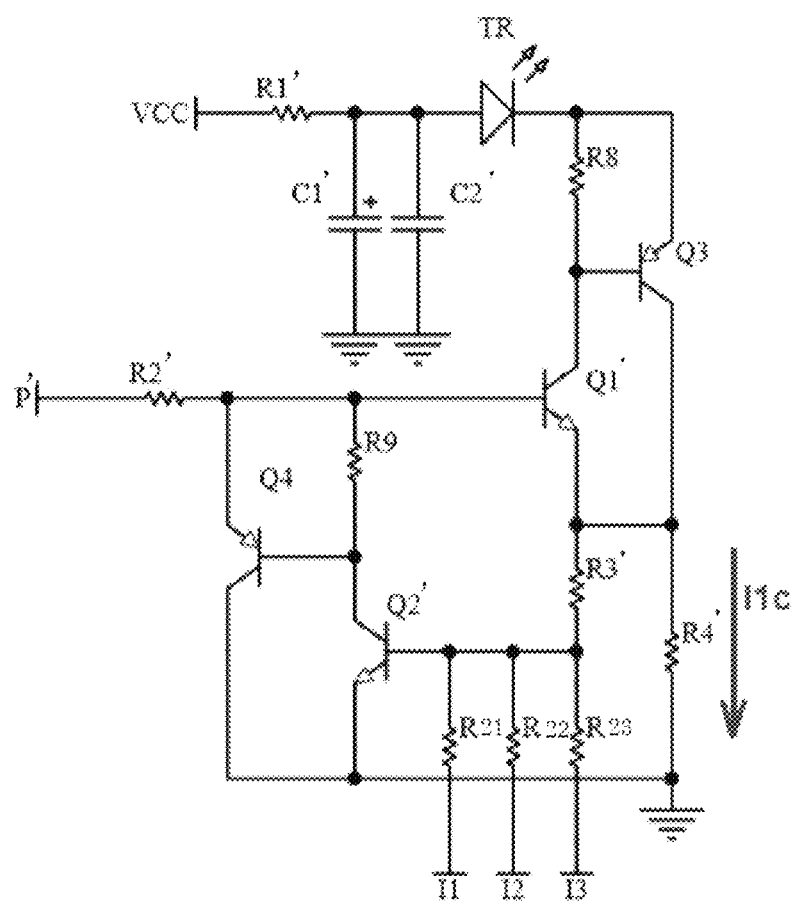
FIGS. 15a and 15b are two optical signal modulation modules of the second type in the embodiment.
Figure 15B:
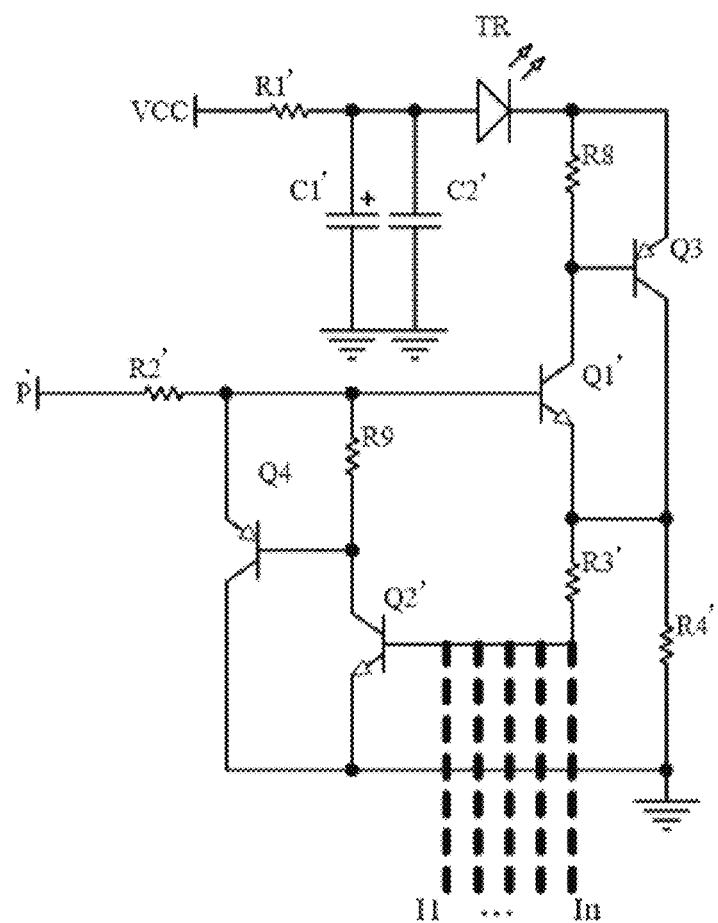
Figure 16A:
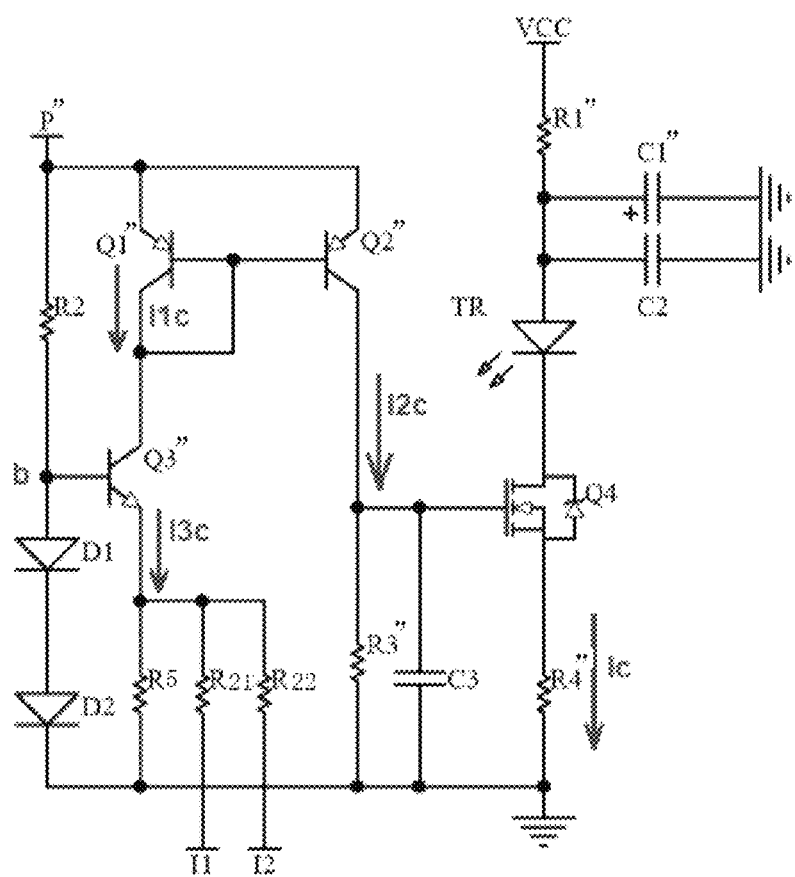
FIGS. 16a and 16b are two optical signal modulation modules of the third type in the embodiment.
Figure 16B:
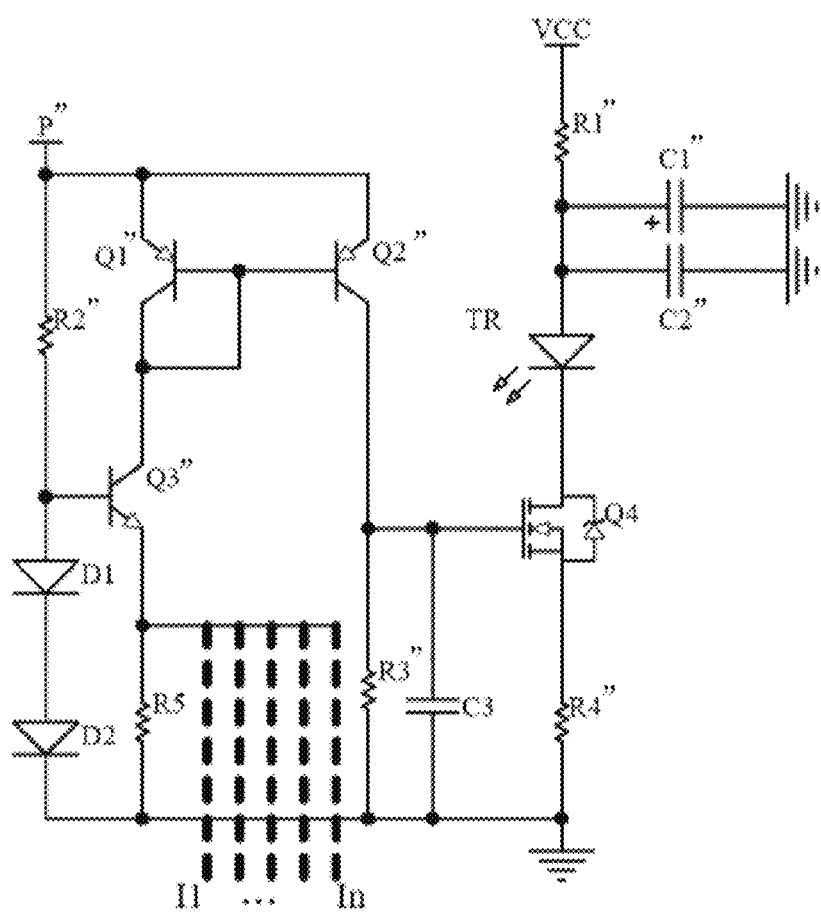
Figure 17A:
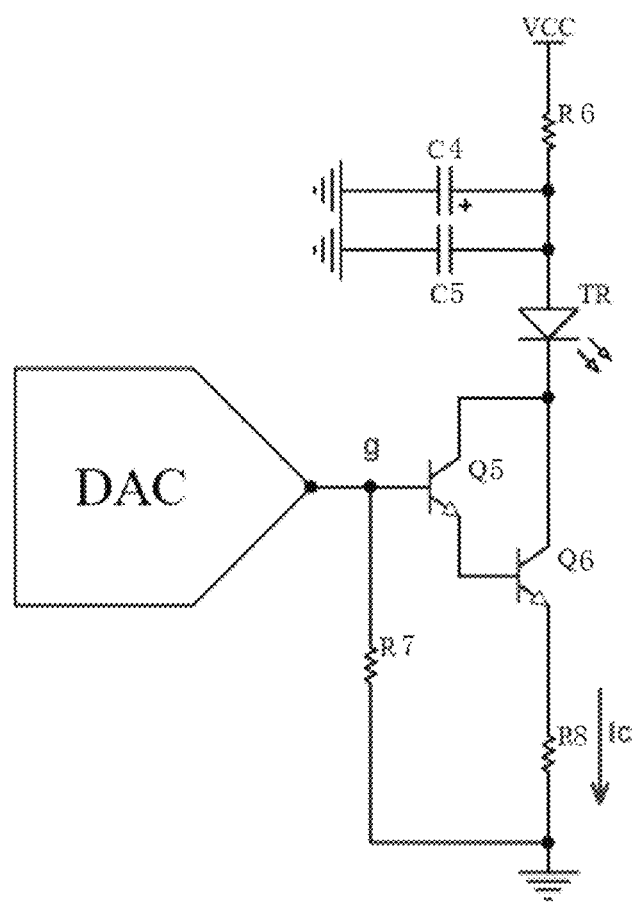
FIGS. 17a and 17b are two optical signal modulation modules of the fourth type in the embodiment.
Figure 17B:
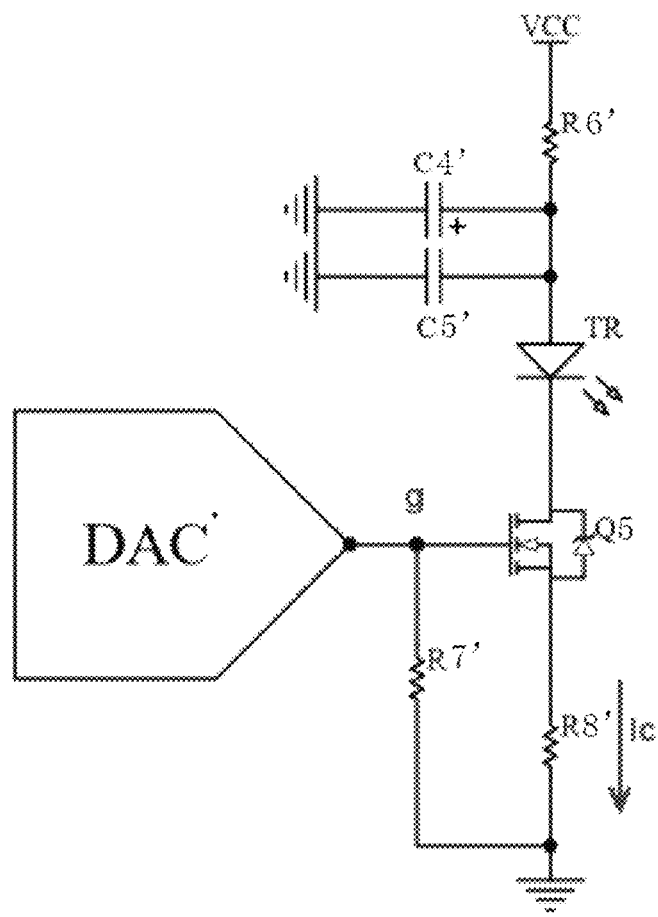
Figure 18A:
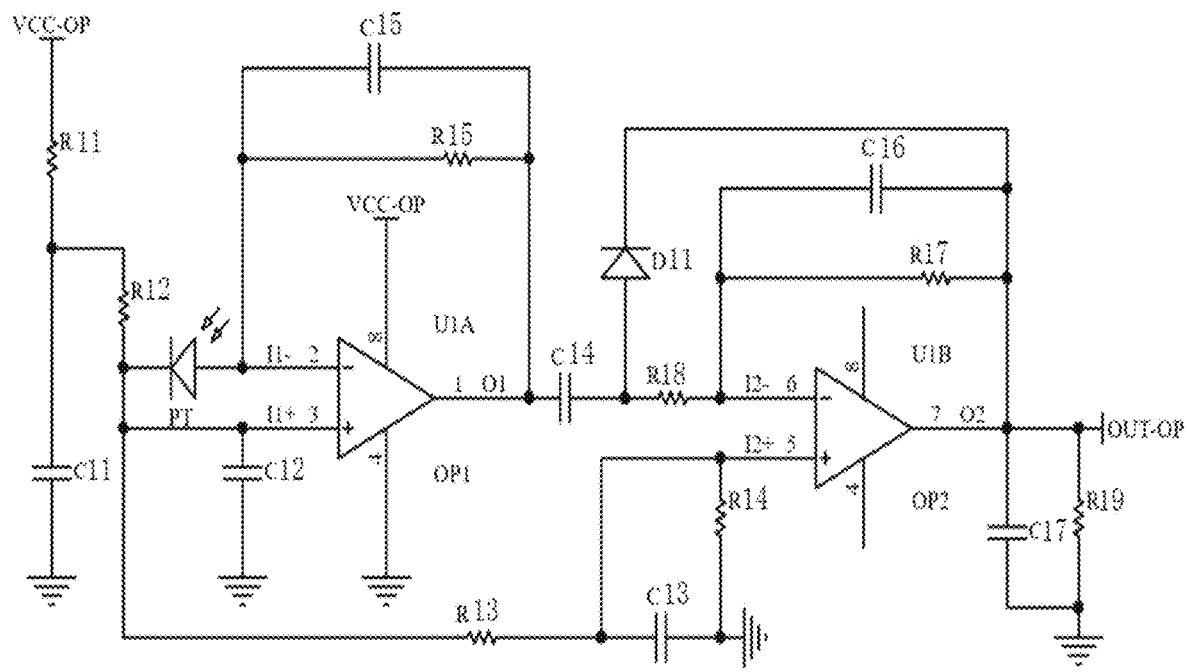
FIG. 18a is a schematic circuit structure diagram (1) of the combination of a voltage dividing module, a photoelectric conversion module, a signal distortion preventing module, and a signal amplification module in the embodiment.
Figure 18B:
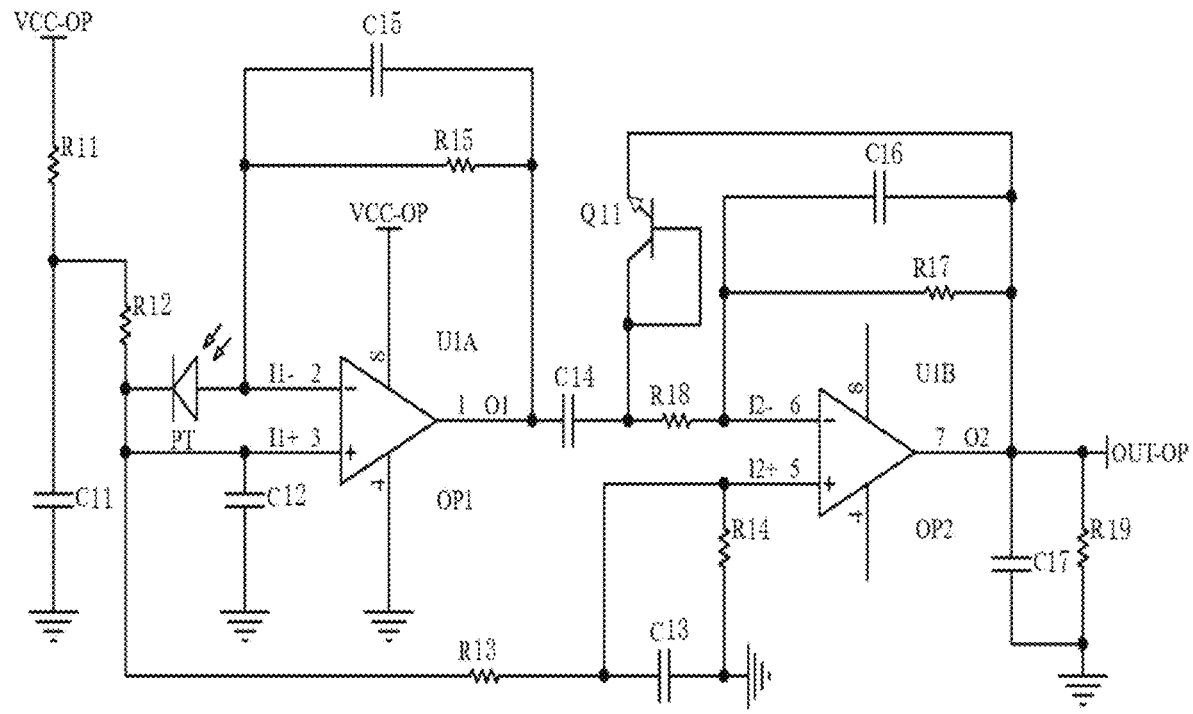
FIG. 18b is a schematic circuit structure diagram (2) of the combination of a voltage dividing module, a photoelectric conversion module, a signal distortion preventing module, and a signal amplification module in the embodiment.
Figure 19A:
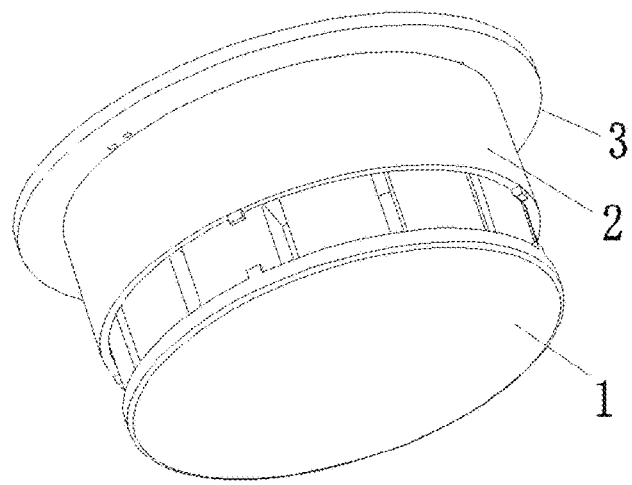
Figure 19B:
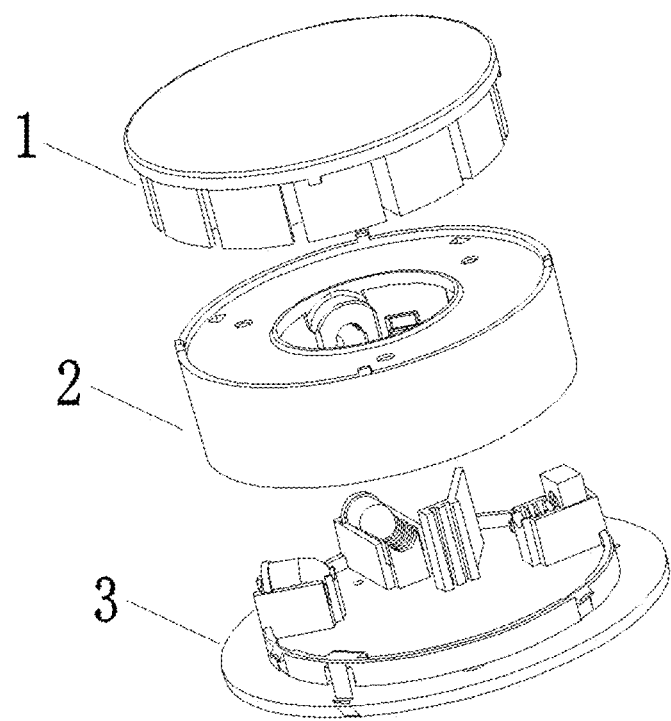
Figure 20A:
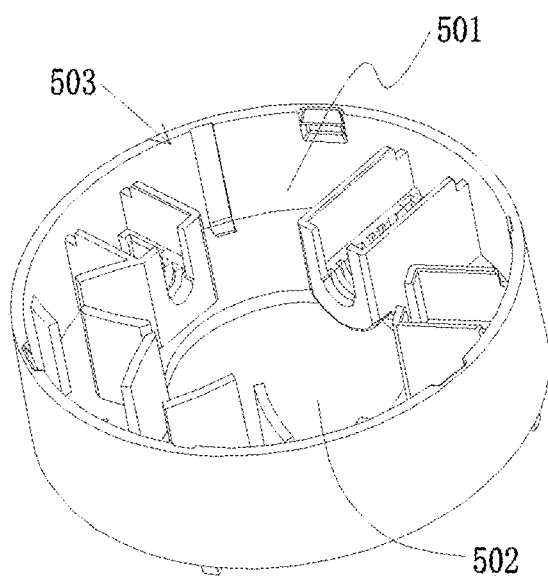
Figure 20B:
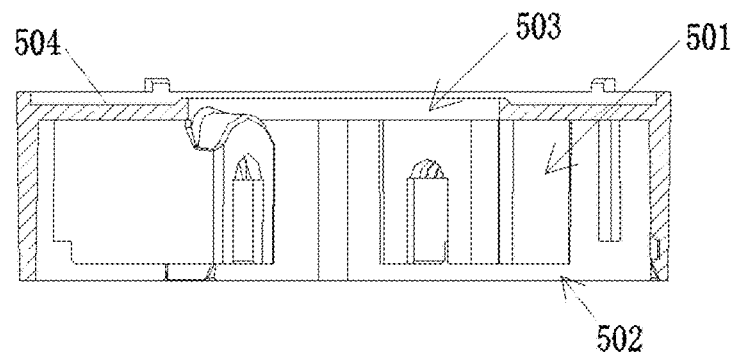

The range of emitting and receiving angles in this embodiment is shown in FIG. 11, in which three angles are marked. And A1, A2, and B are the actual emitting/receiving angle ranges of the first emitting tube 401, the second emitting tube 402, and the receiving tube 403, respectively. Similarly, the emitting tube is not directly fitted to the receiving tube (that is to say, the two can only fit in a scattering manner).

In addition, the above three embodiments all adopt the conventional large-angle emitting tube and the screen to realize scattering fitting between the emitting tube and the receiving tube, but apparently any of the embodiments can also be combined with said emitting angle control. Moreover, as for the plane scattering angles and plane included angles described in the above embodiments, it does not mean that the relevant central optical axes need to be on the same plane but refers to the angle relation on the virtual plane for measuring the included angle between the two optical axes.

Embodiment 4

In order to ensure more effective fire alarm, the detection component also comprises a detection circuit system on the basis of adopting the above-mentioned relevant physical structure. Surely, the detection circuit system can also be independently applied to other photoelectric smoke alarms to fulfill its detection function.

When the detection circuit system is applied to Embodiments 1 to 3 or other variants thereof, it can be used to modulate the optical signals emitted by the two emitting tubes (i.e., the first emitting tube 401 and the second emitting tube 402) so that each current waveforms of the two can have at least one current pulse within the same modulation period. The current pulses emitted by the first emitting tube 401 and the second emitting tube 402 can be independent of each other or can overlap each other. (Independence from each other means the two current pulses have completely different time sequences without any overlapping while overlapping with each other includes exactly the same and at least partial overlapping. In the case of partial overlapping, the overlapping time sequence and width should meet the performance requirements of the receiving tube.) When the current pulses of the two are independent of each other, the receiving tube 403 can separately receive the scattered optical signals of the two, thereby obtaining two light intensity data; when the two overlap with each other, the receiving tube 403 can receive only one scattered light signal, thereby obtaining one light intensity data.

The plane scattering angle between the central axis of the first emitting tube 401 and the central axis of the receiving tube 403 is named scattering angle $\theta 1$ and the plane scattering angle between the central axis of the second emitting tube 402 and the central axis of the receiving tube 403 is named scattering angle $\theta 2$. The angles of $\theta 1$ and $\theta 2$ range from 10° to 55° and from 70° to 140°, respectively. Therefore, the light intensity data obtained by the receiving tube 403 can be counted as the scattered light intensity data of the scattering angle θ1, the scattered light intensity data of the scattering angle θ2, and the scattered light intensity data of the scattering angle θ12, which respectively represent the scattered light intensity data acquired when the first emitting tube 401 acts alone, when the second emitting tube 402 acts alone and when the first emitting tube 401 and the second emitting tube 402 act jointly.

In a preferred case, the first emitting tube 401 and the second emitting tube 402 should each have at least two current pulses within the same modulation period, namely, the first current pulse and the second current pulse. The first current pulses of the two are independent from each other (that is, time sequences are different, or partially overlapping and the overlapping is smaller than the detection requirements of the receiving tube 403 so that it achieves the actual effect of independence of the two current pulses), and the second current pulses are at least overlapping (that is, the time sequences are at least partially overlapping, and the overlapping width meets the detection requirements of the receiving tube 403). Therefore, the scattered light intensities of scattering angle θ1 and scattering angle θ2 are the scattered light intensity values generated respectively when the first current pulses of the first emitting tube 401 and the second emitting tube 402 act alone, while the scattered light intensity of the scattering angle θ12 is the scattered light intensity value generated when the second current pulses of the first emitting tube 401 and the second emitting tube 402 act jointly. That is to say, within one modulation period, the two emitting tubes 401 and 402 emit independently according to a predetermined modulation method, and the receiving tube 403 can receive three scattered light intensity data in this modulation period.

As shown in FIGS. 12-13, 14*a*, 14*b*, 15*a*, 15*b*, 16*a*, 16*b*, 17*a*, 17*b*, 18*a*, and 18*b*, in some preferred embodiments, the detection circuit system comprises a signal modulation module 7, a photoelectric conversion module 4, and a signal amplification module 5. The input end of the photoelectric conversion module 4 is installed with a light receiving module 3. The light modulation module 2 is installed on the signal modulation module 7, the output end of the photoelectric conversion module 4 is connected to the input end of the signal amplification module 5 and the output end of the signal amplification module is connected to the input end of the signal modulation module. The signal modulation module converts the received digital signal into analog signal to modulate the light emitting mode of the light emitting module. The minimum number of the light emitting module 2 is two and other parts are provided accordingly.

Among them, the analog signal emitted by the signal modulation module is received by the light emitting module, the light emitted by the emitting module is received by the light receiving module, the photoelectric conversion module converts the light received by the light receiving module into electrical signal which is sent out to the central processing module 6 of the fire detector after being amplified by the signal amplification module. The light received by the light receiving module is the light emitted by the light emitting module and scattered or reflected via smoke particles or interference sources in the air. The central processing module 6 of the fire detector outputs a level signal (binary digital signal, changing from 0 to 1), and inputs it into the signal modulation module to convert it into an analog signal to modulate the emitting frequency, the current pulse width of each emitting time (light emitting time) and the current value (light intensity). The level signal output by the central processing module 6 modulates the level signal according to the signal output by the signal amplification module (output 0 or 1).

Under certain conditions, the signal modulation module is used to dynamically adjust the intensity of the light emitted by the light emitting module (light emitting tube TR) so that the dynamically-modulated light is reflected and scattered by interference sources (small bugs, hair, spider silk, dust, dirt, oil fume, water vapor, mote and suspended particles) and smoke, etc. The reflected light and the scattered light are received by the light receiving module (light receiving tube PT), and then the received light signal is matched with the photoelectric conversion module and the signal amplification circuit to obtain the reflected light and scattered light signals. The light intensity is a function of the diameter, shape, refractive index, wavelength of light, and the geometry of the photoelectric sensor. The amplified signal is then calculated by the central processing unit in the fire detector based on the Mie scattering theory. And mathematical models and equations are established to solve the light intensity at the scattering angle so as to confirm the characteristics of the smoke particles and thereby identify interference sources such as small bugs, hair, spider silk, dust, dirt, oil fume, water vapor (salt fog), mote (suspended particles), etc., thus effectively reducing false alarms of the detector and improving its alarming accuracy.

The signal modulation module adopts digital level control and the light emitting module adjusts the current. By controlling the current of the current control branch (network labels I1, I2, . . . , In), when I1 is 0, the current of the emitting tube will increase; when I2 is 0, the current of the emitting tube will increase again, and the increase of the current of the emitting tube is equal to the increase of the light intensity; otherwise, the decrease of the current of the emitting tube is equal to the decrease of the light intensity. I1 . . . In in the figure is an extension of the current control branches I1, I2, and I3, and P1, I11, I12, I13, P2, I21, I22 and I23 of the central processing unit are current control branches connected to the control pins of the two emitting circuits which send digital signals to the signal modulation module. VOP pin is connected to VCC-OP and SKS pin is connected to OUT-OP.

In addition, the current pulse width is controlled via the level change time of the level change frequency control terminal P, namely the time from 0 to 1 and 1 to 0, and the number of current pulses is controlled via the level change frequency of the level change frequency control terminal P, namely the change times from 0 to 1 and 1 to 0. In addition, the pulse width is adjusted to meet the signal bandwidth of the circuit and prevent optical signals from being distorted. The number of pulses is used to detect the dynamic characteristics of the particles. In other words, the particle state and quantity of the scattered light and the reflected light are received via the light receiving module to allow the central processing unit to adjust the light emitting time, frequency and the light intensity via the signal modulation module. As a result, three circuit structures are generated, which are shown hereafter.

9. The first embodiment related to a signal modulation module comprises a VCC power supply terminal 1, a resistor R1, a capacitor C1, a capacitor C2, a resistor R2, a triode Q1, a triode Q2, a resistor R3, a resistor R4, and an electrical level change frequency control terminal P. The other end of resistor R1 is connected with the positive electrode of the light emitting module whose negative electrode is linked with the collector of triode Q1. Capacitor C1 and capacitor C2 are connected on the connecting line where the other end of resistor R1 is connected to the positive electrode of the light emitting module. The collector of triode Q2 is connected to the resistor R2 and the base of triode Q1, respectively. The emitter of triode Q1 is connected to one end of resistor R3 and one end of resistor R4, and its base is connected to one end of resistor R2. The emitter of the triode Q2 is connected to the other end of the resistor R4 and grounded. Multiple current control branches are linked to the connecting line where the other end of resistor R3 is connected with the base of triode Q2. The other end of the resistor R2 is connected to the level change frequency control terminal P. Multiple current control branches are lapped via one end of resistors R21, R22 and R23 respectively on the connecting line where the other end of resistor R23 is connected to the base of triode Q2. And the other ends of the resistors R21, R22, and R23 are labeled I1, I2, and I3. The level change frequency control terminal P is connected to the digital level control terminal P1 and the digital level control terminal P2 of the central processing unit 6 in the fire detector.

When the level change frequency control terminal P inputs a high level, the triode Q1 is conducted, and the current I1c flows through the resistor R4, which causes the voltage at the two ends of resistor R4 to rise. When the voltage exceeds 0.7V, Q2 is conducted, which causes voltage at the base of the triode Q1 to drop. The decrease of the current I1b leads to the decrease of current I1c, forming a negative feedback circuit, in which Q1 and Q2 are in an amplified state. $I1c \approx 0.7*[(R21//R22//R23)+R3]/(R21//R22//R23)/R4$. At this time I1, I2, I3 are 0, and the signals with I1, I2, I3 being 0 and I1, I2, I3 being 1 are all controlled and input by the central processing unit 6 of the fire detector.

The second embodiment related to the signal modulation module comprises a VCC power supply terminal 2, a resistor R1', a capacitor C1', a capacitor C2', a resistor R2', a resistor R8, a resistor R9, a triode Q1', a triode Q2', a triode Q3, a triode Q4, a resistor R3', a resistor R4' and an electrical level change frequency control terminal P'. The VCC supply terminal 2 is connected with one end of resistor R1'. Capacitor C1' and Capacitor C2' are connected on the connecting line where the other end of resistor R1' is connected with the positive electrode of the light emitting module. The negative electrode of the light emitting module is connected with one end of the resistor R8 and the emitter of triode Q3. The base of the triode Q3 is connected to the other end of the resistor R8 and the collector of the triode Q1', and the collector is respectively connected to one end of the resistor R4', one end of the resistor R3' and the emitter of the triode Q1. The base of triode Q1' is respectively connected to one end of resistor R9, the emitter of triode Q4 and resistor R2'. The base of triode Q4 is respectively connected to the other end of resistor R9 and the collector of triode Q2'. The collector, the emitter of triode Q2' and the other end of resistor R4 are grounding connected. Multiple current control branches are connected to the connecting line where the base of triode Q2' is linked with the other end of resistor R3'. The other end of resistor R2' is connected with the electrical level change frequency control terminal P'. Multiple current control branches are lapped via one end of resistors R21, R22 and R23 respectively on the connecting line where the other end of resistor R23 is connected to the base of triode Q2. And the other ends of the resistors R21, R22, and R23 are labeled I1, I2, and I3. The level change frequency control terminal P' is connected to the digital level control terminal P1 and the digital level control terminal P2 of the central processing unit 6 in the fire detector.

This solves the technical problem that the first type signal modulation module having only the triode Q1' and triode Q2' does not have a large amplification factor (β), resulting in poor dynamic characteristics of the circuit. Therefore, triode Q1 is connected in parallel to the side of triode Q1'. Triode Q4 is connected in parallel to the side of triode Q2', and triode Q1' and triode Q3 form a Darlington tube, and triode Q2' and triode Q4 also form a Darlington tube, which improves amplification factor (0) to make dynamic modulation performance better. $I1c \approx 0.7*[(R21//R22//R23)+R3']/(R21//R22//R23)/R4'$. At this time I1, I2 and I3 are 0.

The third embodiment related to the signal modulation module comprises a VCC power supply terminal 3, a resistor R1", a resistor R2", a resistor R3", a resistor R4", a resistor R5, a capacitor C1", a capacitor c2", a capacitor C3, a triode Q1", a triode Q2", a triode Q3", a field effect transistor Q4, a diode D1, a diode D2 and a level change frequency control terminal P'". The VCC power supply terminal 3 is connected to one end of the resistor R1" of which the other end is connected to the positive electrode of the light emitting module. The capacitor C1" and the capacitor C2" are connected on the connecting line where the other end of resistor R1" is connected to the positive electrode of the light emitting module. The negative electrode of the light emitting module is connected to the drain of the field effect transistor Q4. The grid electrode of the field effect transistor Q4 is connected to one end of the capacitor C3, one end of the resistor R3 and the collector of the triode Q2" respectively, and its source electrode is connected to one end of the resistor R4". The emitter of triode Q2" is connected to the emitter of triode Q1" and the level change frequency control terminal P'" respectively, and its base is connected to the base and collector of triode Q1". The collector of triode Q1" is also connected to the collector of triode Q3". The base of triode Q3" is connected to one end of resistor R2" and the anode of diode D1, and multiple current control branches are connected to the connecting line where its emitter is linked with one end of resistor R5. Diode D1 and diode D2 are connected in series with each other, and the anode of diode D2 is connected to the other end of resistor R5, the other end of resistor R3", the other end of capacitor C3, and the ground terminal. The resistor R4" is also connected to the ground terminal. The other end of the resistor R2" is connected to the level-change frequency control terminal P'". Multiple current control branches are lapped via one end of resistor R21 and one end of R22 on the connecting line where the other end of the resistor R3" and the base of the triode Q2" are connected. And the other ends of the resistors R21 and R22 are labeled I1 and I2. The level change frequency control terminal P'" is connected to the digital level control terminal P1 and the digital level control terminal P2 of the central processing unit 6 in the fire detector.

Q1 and Q2 constitute a mirror current circuit, and Vb is clamped in series by D1 and D2 to form a reference voltage of about 1.4V. Obviously, $I2c \approx I1c \mp I3c$; so $Ic \approx [(Vb-0.7)*R3/(R21//R22)-Uon]/R4$. At this time I1 and I2 are 0 and Uon is the minimum opening voltage of Q4. Moreover, signals with I1, I2 being 0 and I1, I2 being 1 are controlled input by the central processing unit MCU of the fire detector.

The above are three circuit structures for adjusting light emitting time, emitting frequency, and light intensity according to the state and quantity of particles of the received scattered light and reflected light.

In addition, the light emitting module can also be controlled by pulses to achieve a fourth signal modulation module that dynamically adjusts the light emitted by the light emitting module. It can also have the following two specific structures:

1) The signal modulation module comprises a VCC power supply terminal 4, a digital analog conversion module DAC, a capacitor C4, a resistor R6, a resistor R7, a resistor R8 and a Darlington transistor (composed of triode Q5 and triode Q5). The VCC supply terminal 4 is connected with one end of resistor R6 of which the other end is connected with the positive electrode of light emitting module. Capacitor C4 and capacitor C5 are connected on the connecting line where the other end of resistor R6 is connected with the positive electrode of light emitting module. The negative electrode of light emitting module is connected with the collector of Darlington transistor. The base of Darlington transistor is respectively connected to one end of resistor R7 and the digital analog conversion module DAC. Its emitter is connected with one end of resistor R8. The other end of resistor R7 and the other end of resistor R8 are connected to each other and then grounded.

2) The signal modulation module comprises a VCC power supply terminal 4, a digital analog conversion module DAC', a capacitor C4', a capacitor C5', a resistor R6', a resistor R7', a resistor R8' and a field effect transistor Q5. The VCC supply terminal 4 is connected to one end of resistor R6'. The other end of resistor R6' is connected to the positive electrode of light emitting module. Capacitor C4' and capacitor C5' are connected on the connecting line where the other end of resistor R6' is connected to the positive electrode of light emitting module. The negative electrode of the light emitting module is connected to the drain of the field effect transistor. The grid electrode of the field effect transistor is respectively connected to one end of the resistor R7' and the digital analog conversion module DAC'. Its source electrode is connected to one end of resistor R8'. The other end of resistor R7' and the other end of resistor R8' are connected to each other and then grounded.

The above two signal modulation modules make the DAC module generate different analog voltage Vg, duty cycle and frequency through the program recorded by the central processing unit, thereby adjusting the current, pulse width and number of pulses of the emitting tube. Hence $Ic \approx (Vg-1.4)/R8$; or $Ic \approx (Vg-Uon)/R8$. Uon is the minimum opening voltage of Q4. The pulse width is adjusted to meet the signal bandwidth of the circuit and prevent the optical signal from being distorted. The number of pulses is adopted to detect the dynamic changing characteristics of particles. And the digital analog conversion module DAC is connected to the digital level control terminal P1 and the digital level control terminal P2 of the central processing unit 6.

The structure and principle of the photoelectric conversion module and the signal amplification module working together are as follows:

The photoelectric conversion module comprises an operational amplifier OP1, a resistor R15, and a capacitor C15, in which the input terminal I1− and the input terminal I1+ of the operational amplifier OP1 are respectively connected to both ends of the light receiving module. The two ends of the resistor R15 are respectively connected to the input terminal I1− and the output terminal O1 of the operational amplifier OP1. The capacitor C15 and the resistor R15 are connected in parallel.

Signal amplification module operational amplifier OP2, resistor R17 and capacitor C16; the two ends of resistor R17 are respectively connected to the input terminal I2− of operational amplifier OP2 and the output terminal O2 of operational amplifier OP2. Capacitor C16 and resistor R17 are connected in parallel, and the input terminal I2+ of operational amplifier OP2 is lapped with the voltage dividing module.

A signal distortion preventing module is also provided. The output end of the photoelectric conversion module is connected to the input end of the signal amplification module through the signal distortion preventing module. The signal distortion preventing module uses a diode D11 or a triode Q11. An output end O1 of the operational amplifier OP1 is connected to Capacitor C14, and the input terminal I2− of the operational amplifier OP2 is connected to the resistor R18. The positive electrode of the diode D11 is connected to the connecting line where the capacitor C14 and the resistor R18 are connected, and its negative electrode is connected to one end of the capacitor C16. The collector of the triode Q7 is connected to the connecting line where the capacitor C14 and the resistor R18 are connected, and its emitter is connected to one end of the capacitor C16 and its base is connected to the emitter.

A voltage dividing module is also provided. The voltage dividing circuit is connected to the photoelectric conversion module and the signal amplification module, respectively. The voltage dividing module includes voltage input end VCC-OP, resistor R11, resistor R12, resistor R13 and resistor R14. Resistor R11, resistor R12, resistor R13 and resistor R14 are connected in series with each other. The input terminal I1+ of the operational amplifier OP1 and the negative electrode of the light receiving module are lapped on the connecting line where the resistor R12 and the resistor R13 are connected to each other. The resistor R14 is connected to the input terminal I2+ of the operational amplifier OP2. The voltage of the voltage input end VCC-OP is generally 3V or 3.3V, and the working voltage is 1.8-3.6V.

The voltage dividing module provides the in-phase terminals I1+ and I2+ of the operational amplifiers OP1 and OP2 with different input voltages. By adjusting the resistance of the four resistors of the voltage dividing module, the voltage of I1+ is much larger than the voltage of I2+ (the voltage of I2+ approximating D1 forward-conducting voltage, or normal conducting voltage of Q1). Generally, I1+ is close to VCC-OP, while I2+ is between 0.2V-0.5V, which makes the output voltage of O1 much larger than the voltage of I2−. The coupling capacitor C8 passes the diode D11 or the triode Q11 fast charging in one direction, and the circuit stabilization time is about 2 ms. Capacitor C14, R18, and R17 form a discharge circuit. The discharge time determines the signal bandwidth. The time of the signal pulse width is more than 200 us, ensuring that the optical signal is not distorted. The conflict between the circuit stabilization time and the signal bandwidth is resolved, and the problem of optical signal distortion resulting from the longer photoelectric conversion time caused by the capacitance characteristics of the photodiode PN junction is also solved.

The circuit structure of the detection system above is designed to meet the detection requirements of the new optical maze, so that it can identify the size, density and spatial distribution of particles, such as dust, dirt, oil fume, water vapor (salt fog), mote (suspended particles), smoke, etc. After the detected light is reflected or scattered by the smoke particles, the reflected and scattered light intensity is acquired via the photoelectric conversion module and the signal amplification module. The light intensity is a function of the diameter, shape, refractive index, wavelength of light, and the geometry of the photoelectric sensor. Then mathematical models and equations are established based on the Mie scattering theory to solve the light intensity at the two scattering angles so as to confirm the characteristics of the smoke particles and thereby identify interference sources such as small bugs, hair, spider silk, dust, dirt, oil fume, water vapor (salt fog), mote (suspended particles), etc., thus effectively reducing false alarms of the detector and improving its alarming accuracy. Meanwhile, the photoelectric conversion module and the signal amplification module also have the following features: short circuit stability time, wide signal bandwidth, and no distortion of the optical signal.

Embodiment 5

As shown in FIGS. 19a, 19b, 20a, 20b, and 21-27, a new type of photoelectric smoke and fire alarm is mainly formed by the combination of a detector and an optical maze 1. The optical maze 1 includes a base 100. The side of the base 100 near the detector is provided with a maze portion, and the detector is fitted on this side to form a complete alarm.

As shown in FIGS. 19a, 19b, 20a, and 20b, said detector includes a detection component 3 for detection and an upper cover 2 for accommodating the detection component. The detection component adopts any one of the detection components for Photoelectric Smoke Detection Fire Alarm in embodiments 1-3. The inside of the upper cover 2 is hollow to form a detection cavity 501, and at least a part of the detection component is accommodated in the detection cavity 501. The upper cover 2 has a first opening 502 and a second opening 503. At least a part of the detection component is accommodated in the detection cavity 501 via the second opening 503. The second opening 503 is fitted to the bottom plate 400. The first opening 502 and the optical maze 1 are fitted to allow outside smoke to pass through the optical maze and enter the detection cavity 501 to be detected by the detection component. Although FIGS. 19a, 19b, 20a, and 20b show that the detection component 3 is accommodated in the detection cavity 501 of the upper cover 2 except the bottom plate 400, and the alarm is fixed as a whole by the bottom plate 400 of the detection component 3, it does not indicate that this is the only method. Other similar methods such as fixing the alarm integrally via the upper cover 2 with the detection component 3 fully contained in the detection cavity 501 are also feasible.

As shown in FIGS. 19a, 19b, 20a, and 20b, the overall shape of the upper cover 2 can be a hollow cylinder, its lower surface vacant to form a second opening 503, its central area of the upper surface vacant to form a first opening 502, and its hollow cavity inside as the detection cavity 501. Meanwhile, a ring-shaped supporting disk 504 is provided outside the first opening 502 on the upper surface to set the maze portion of the base 100. The fitting of the supporting disk 504 to the lower surface of the maze portion can significantly avoid outside light and smoke from contacting the detection cavity, so that they will be only detected after entering the detection cavity 501 through the maze portion.

The maze portion has a maze passage 300. Without considering connectivity of the maze passage 300, the overall cross-sectional shape of the maze portion may preferably be shapes with closed boundary such as circle, polygon or oval. That is to say, the inside and outside of the maze part can only communicate through the maze passage 300.

The maze passage 300 is formed by pairing of a first blocking part 301 and a second blocking part 302. The first blocking part 301 includes a first ridge 311 and a second ridge 312, and the second blocking part 302 includes a third ridge 313 and a fourth ridge 314. The angle between third ridge 313 and the fourth ridge 314 is an acute angle, 30-60° being preferable and 45° the best. The angle between the third ridge 313 and the fourth ridge 314 is 45-120°. In addition, after the first blocking part 301 and the second blocking part 302 are fitted, the fourth ridge 314 extends into a region between the first ridge 311 and the second ridge 312.

Optimally, the fourth ridge 314 is extended to or near a junction between the first ridge 311 and the second ridge 312 to form a maze passage in a Z shape or similar to a Z shape. In principle, the position to which the fourth ridge 314 extends between the first ridge 311 and the second ridge 312 can be varied, but considering the actual effect, the best solution is to extend the fourth ridge 314 to or near the joint of the two as this can minimize the interference of the external light to the detection component without affecting the gas circulation effect. In this case, the tail of the fourth ridge 314 can be disposed in parallel to the second ridge 312 to form a parallel part 3141 to reduce the adverse effect on the gas passage.

The optimum cross section shapes of said first ridge 311, second ridge 312, third ridge 313 and fourth ridge 314 can be straight line, arc, curve, etc. The first blocking part 301 and the second blocking part 302, after manufactured respectively, may be fitted on the base 100 through welding, bonding, clapping, etc., or may be integrally formed with the base 100, which is a better alternative. To ensure the gas exchange effect inside and outside, the narrowest width of the maze passage 300 should not be less than 1 mm. That is to say, the distance between the front end of the first ridge 311 and the third ridge 13 as well as the distance between the tail of the fourth ridge 314 and the first ridge 311 or the second ridge 312 should not be less than 1 mm to ensure a sufficient gas exchange effect inside and outside the fire alarm. More preferably, the narrowest width of the maze passage 300 is not less than 3 mm.

Figure 21:
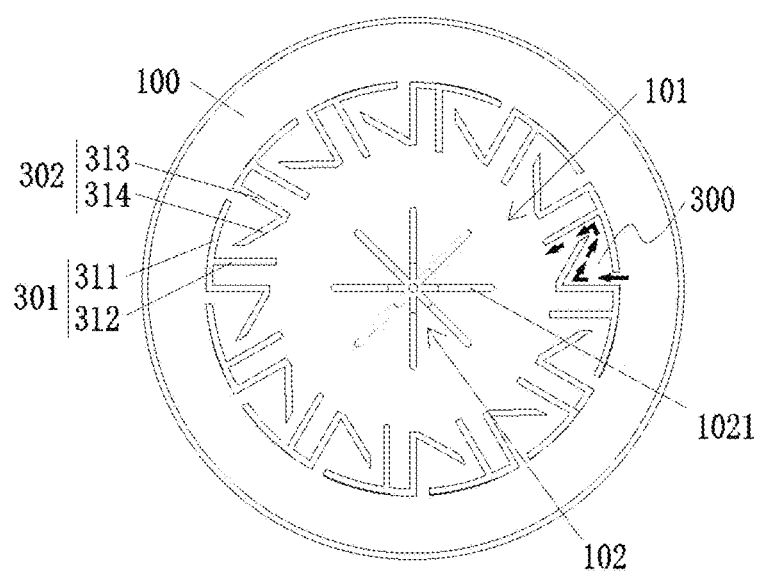
FIG. 21 is a schematic plan view of the structure of the optical maze in certain embodiment of the present invention. In order to ensure the closure effect of the maze portion, a connection portion is set between the first blocking part and the second blocking part that form each maze passage, so that outside the maze passage, the maze portion is sealed on the whole. The black arrow represents the schematic diagram of the outside gas entering the chamber.
Figure 22:
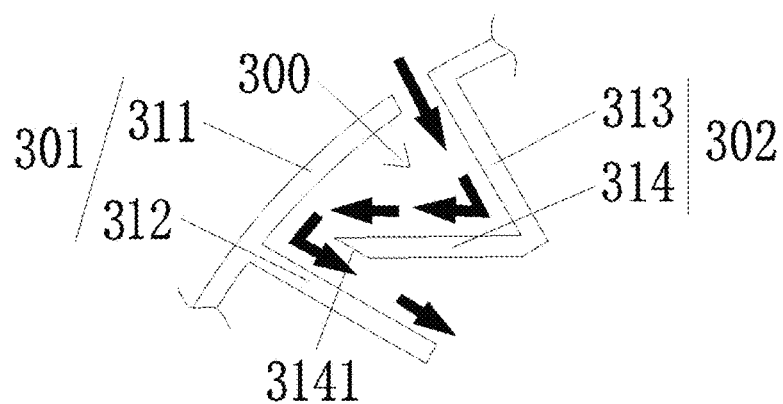
FIG. 22 is an enlarged schematic view of the structure of the maze passage in FIGS. 20a and 20b, wherein a black arrow indicates the flow direction of outside gas.
Figure 23:
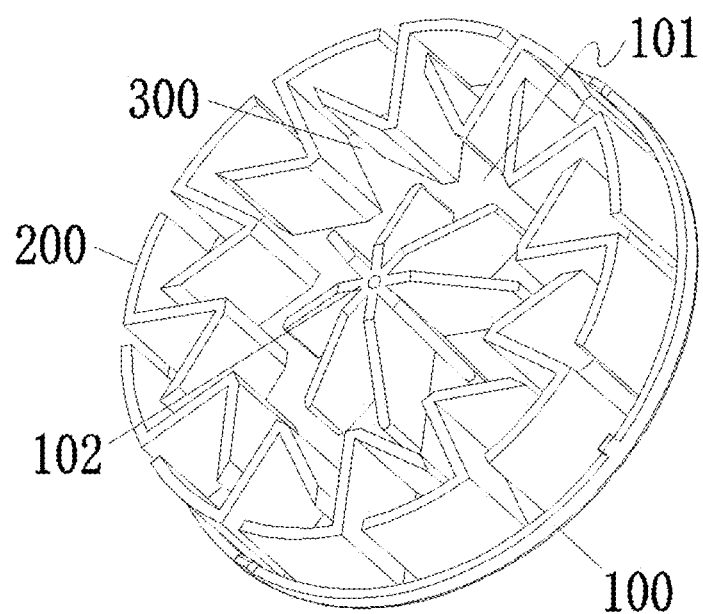
FIG. 23 is a schematic three-dimensional structure diagram of the optical maze in the embodiment of FIGS. 19a and 19b.
Figure 24:
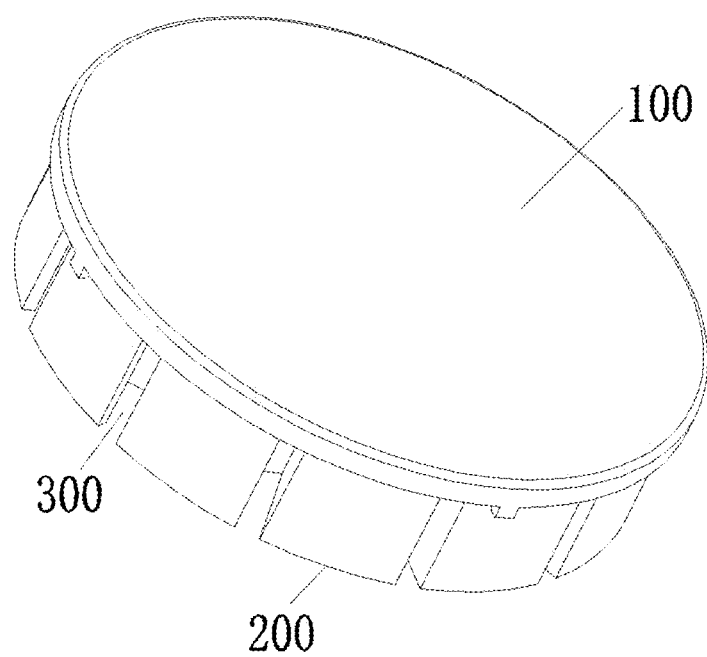
FIG. 24 is a schematic structural diagram of the rear in FIG. 23.
Figure 25:
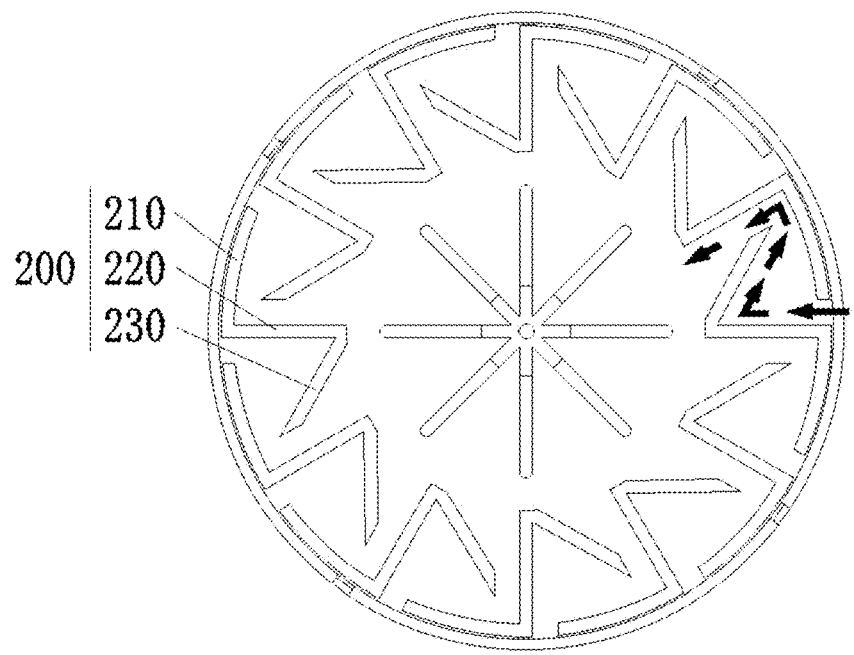
FIG. 25 is a schematic front top view of FIG. 23, wherein the black arrow represents a schematic view of outside gas entering the chamber.
Figure 26:
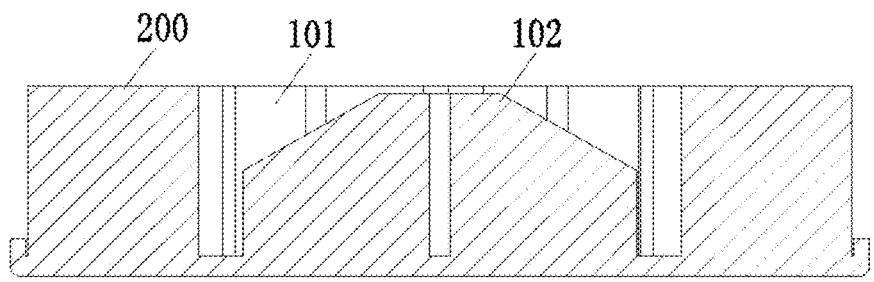
FIG. 26 is a sectional view of FIG. 23.
Figure 27:
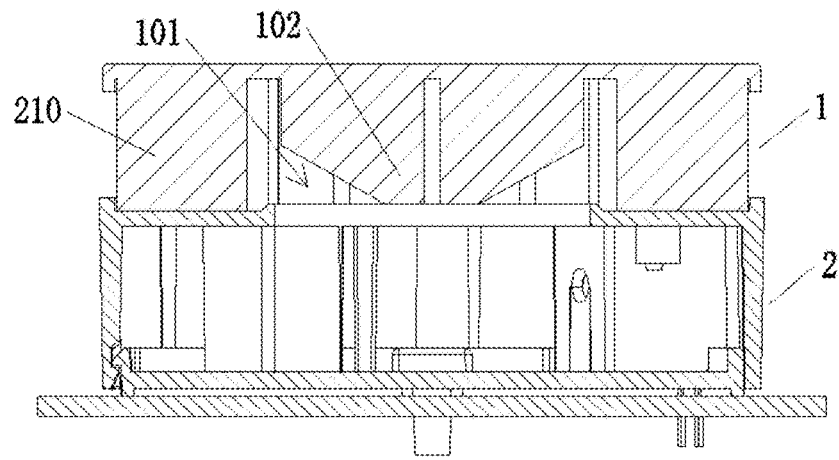
FIG. 27 is a schematic section of the combination of the optical maze and the detection component in the embodiment of FIGS. 19a and 19b, wherein the upper part is optical maze 1, and the lower part is upper cover 2 and detection component 3.
Figure 28:
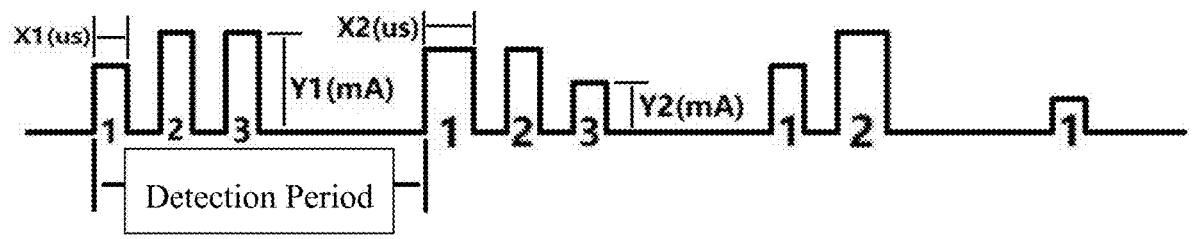
FIG. 28 is a schematic diagram of impulsive current in an embodiment of the present invention.
Figure 29A:
FIGS. 29a-29c are schematic diagrams of impulsive current in other embodiments of the present invention, i.e.
Figure 29B:
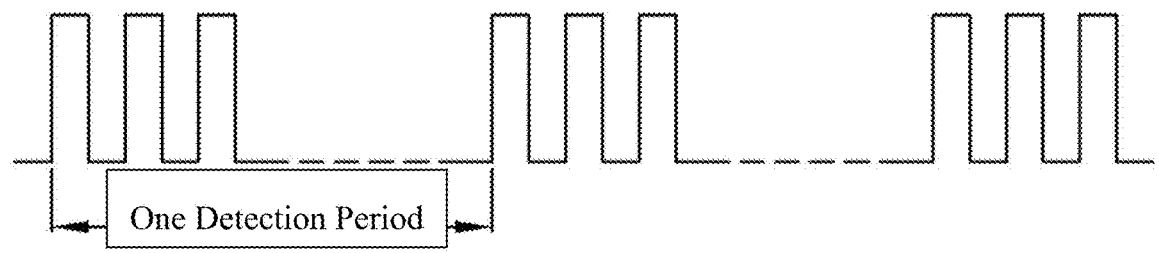
Figure 29C:
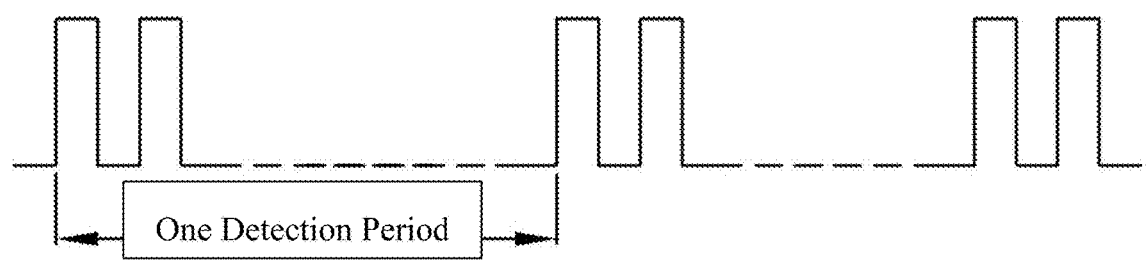

In addition, a connecting portion may be provided between the first blocking part 301 and the second blocking part 302 of each maze passage 300, so that the maze portion except the maze passage is sealed as a whole. For example, as shown in FIG. 21, the second blocking part 302 of 300 is connected to the first blocking part 301 of the maze passage behind to close the gap therebetween, forming a basic component unit similar to a "n" shape.

In some cases, the optical maze further includes a cavity 101, which is in connectivity with the detection component. And the cavity 101 is disposed at the center position of the maze portion in a closed shape (only referring to a relative position, not the "center point" or "central area" in the traditional sense), so that the chamber 101 can communicate with the outside through the maze passage 300.

In order to prevent the external gas (that is, to-be-detected ambient gas) from directly flowing out from the maze passage 300 on the other side to reduce the detection effect after it enters the maze passage 300 from one side of the maze and passes through the chamber 101 (of course, which can also flow out from the maze passage 300 in another direction), a guide member 102 can be disposed in the chamber 101, which includes a number of guide vanes 1021 to make the external gas change the direction to flow towards the detection component along the axis of the optical maze after it enters the chamber 101. Meanwhile, such a change can also greatly reduce the interference of the external light with the detector.

In other preferred cases, the maze passage 300 may be formed by two adjacent maze blocks 200 arranged at intervals. Each maze block 200 has the same structure, including head ridge 210, middle ridge 220 and tail ridge 230. Head ridge 210 and tail ridge 230 are respectively disposed at or near the two ends of middle ridge 220, and the two directions are different. For example, the first ridge 210 extends from one end of the second ridge 220 to the right thereof and the third ridge 230 extends from the other end of the second ridge 220 to the left thereof.

The maze block 200 can be regarded as further optimization of the basic composition unit similar to a "π" shape, and the first ridge 311 of the first blocking part 301 and the third ridge 313 of the second blocking part 302 are overlapped to form one part.

The maze blocks 200 are disposed on the surface of the base 100 in circles and at intervals in a circumferential direction, and the maze block 200 are disposed on the base 100 in the same orientation. Since the maze blocks 200 have a certain height, an annular protruding structure is formed on the side surface of the base 100, and a chamber 101 is formed in the center of the circle.

The included angle between the middle ridge 220 and the tail ridge 230 is an acute angle, and the tail ridge 230 of the previous maze block 200 is extended near a junction of the head ridge 210 and the middle ridge 220 of the next maze block 200, thus forming a maze passage 300 therebetween. The middle ridge 220 and the tail ridge 230 of the previous maze block 200 form a third ridge 313 and a fourth ridge 314 of the second blocking part 302 respectively, and the head ridge 210 and the middle ridge 220 of the next maze block 200 form a first ridge 311 and a second ridge 312 of the first blocking part 301 respectively.

The overall cross-sectional shape of the maze portion is circular, the cross-sectional shape of head ridge 210 is arc-shaped, and the cross-sectional shapes of middle ridge 220 and tail ridge 230 are both line-shaped.

In addition, in the above embodiments, the first blocking part 301 and the second blocking part 302 forming the maze passage 300 or the adjacent maze block 200 all make the closed geometric shape excluding the maze passage 300 in a circular manner, but this does not mean that the optical maze must be designed so. Another alternative is to set the first blocking part 301 and the second blocking part 302 or the maze block 200 only in several directions and connect them via connecting structure. In this way, the object of the present invention can also be achieved, but the ventilation efficiency is reduced. For example, for a square-shaped maze portion, a maze passage group of a certain length may be set only at four vertices or at the center of the four sides. Moreover, the arrangement of the maze passage 300 is not limited to the circular way, and may be other methods such as arraying.

The detection component, the detection system and the fire alarm of the present invention can be applied to the existing Photoelectric Smoke Detection Fire Alarm to reduce the size and improve the accuracy. They can be optimally accompanied by the following detection methods.

A new alarming method for the Photoelectric Smoke Detection Fire Alarm comprises at least the following steps:

Step 1: The data acquisition step to acquire the scattered light intensity data of the sample. The data can be obtained through an additional detection unit or from the outside of the system via a data interface. For example, the scattered light intensity data of each sample is continuously collected from the receiving tube 403 of the detection component, and the scattered light intensity data of each sample includes the scattered light intensity at the scattering angle θ1 and the scattered light intensity at the scattering angle θ2. On this basis, other scattered light intensity data may also be included, such as the scattered light intensity data of the scattering angle θ12.

In order to improve the detection and alarm efficiency of this method, in step 1, the sample type may specifically include the fire samples and the interference source samples, wherein the fire samples are used as reference samples and the interference source data is used to exclude interference so that early warning is achieved by processing the fire sample data and interference is eliminated by processing the interference source samples. It is needless to say that the interference source samples are not indispensable but only complementary for the purpose of reducing false alarm rate. Meanwhile, when the sample form is obtained in step 3, the sample form should cover the sample parameters of each sample accordingly, and the comparison of any interference source sample with the sample form should not meet any of the fire categories.

Step 2: The step of data analysis to calculate each sample data and the scattered light intensity data acquired in the previous step to obtain the sample parameters of each sample. The sample parameters include at least one of the following: particle size d, refractive index m, smoke rising slope l, smoke increment y, smoke concentration a, and smoke curvature k.

The particle diameter d and the refractive index m can be calculated according to the following steps:

The scattered light intensity IS satisfying: Is=Ir+Il;

where Ir and Il denote quantities perpendicular to and parallel to a scattering surface respectively, and satisfy:

$$I_r = \frac{1}{k^2 r^2}|S_1(\theta)|^2 I_{r0} = \frac{\lambda^2}{4\pi^2 r^2}|S_1(\theta)|^2 I_{r0} = \frac{\lambda^2}{4\pi^2 r^2} i_1(\theta) I_0 \sin^2\varphi \quad \text{(formula 1)}$$

$$I_l = \frac{1}{k^2 r^2}|S_2(\theta)|^2 I_{l0} = \frac{\lambda^2}{4\pi^2 r^2}|S_2(\theta)|^2 I_{l0} = \frac{\lambda^2}{4\pi^2 r^2} i_2(\theta) I_0 \cos^2\varphi$$

In the above formulas,
$i(\theta,\varphi)=|S(\theta,\varphi)|^2$ is an intensity function and is deduced from the following formula:

$$I_s = \frac{|S(\theta,\varphi)|^2}{k^2 r^2} I_0 = \frac{i(\theta,\varphi)}{k^2 r^2} I_0 \quad \text{(formula 2)}$$

i1(θ) and i2(θ) are respectively:

$$i_1(\theta) = |S_1(\theta)|^2 = \left|\sum_{l=1}^{\infty} \frac{2l+1}{l(l+1)}(a_l\pi_l + b_l\tau_l)\right|^2 \quad \text{(formula 3)}$$

$$i_2(\theta) = |S_2(\theta)|^2 = \left|\sum_{l=1}^{\infty} \frac{2l+1}{l(l+1)}(a_l\pi_l + b_l\tau_l)\right|^2$$

wherein αl and bl are:

$$a_i = \frac{\psi_l(\alpha)\psi_l'(\beta) - m\psi_l'(\alpha)\psi_l(\beta)}{\zeta_l^{(1)}(\alpha)\psi_l'(\beta) - m\zeta_l^{(1)\prime}(\alpha)\psi_l(\beta)} \quad \text{(formula 4)}$$

-continued $$b_i = \frac{m\psi_i(\alpha)\psi'_i(\beta) - \psi'_i(\alpha)\psi_i(\beta)}{m\zeta_i^{(1)}(\alpha)\psi'_i(\beta) - \zeta_i^{(1)'}(\alpha)\psi_i(\beta)}$$

α and β satisfy:

α=πd/λ;

β=mα;

in the above formulas, θ denotes a scattering angle, ϕ denotes an azimuth angle, r denotes a distance, λ denotes a detected light wavelength, all of which are known parameters, and then the particle size d and the refractive index m can be obtained by iterative calculation according to an inverse order of the above formulas in combination with the scattered light intensity IS (calculating α and β after determining d and m, calculating in the order of formula 4321).

In order to make the calculation more accurate, this method may further include the step of correcting the light intensity, namely first measuring the light intensity of the emitting tube with a calibrated instrument to obtain the actual initial light intensity I0, and then using the actual measured initial light intensity I0 to calculate relevant sample parameters, thereby increasing the accuracy of detection and alarm.

Step 3: The step of generating a sample table. As for the sample parameters of each sample calculated in the previous step, a certain parameter (for example, particle diameter d) is used as a measurement index to form a number of fire categories, and the value or value ranges of each sample parameter for each fire category are determined to generate a sample table. And the sample table should cover sample parameters of all samples. In other words, any fire sample parameter, when compared with the sample table, can fall into one and only one fire category. If the previously collected samples also include interference source samples, then any interference source samples, when compared with the sample table, should not fall into any of the fire categories.

The process of forming the sample table is similar to the sorting of a multi-parameter table. In principle, it is necessary to take at least one parameter as an index, such as the particle size d. However, it is also feasible to use multiple parameters at the same time, that is, if the former parameter is the same or similar, the second parameter can be further selected for subdivision and sorting to finally form a sample table.

The sample format of the method (Method 1) is: a particle size d, a refractive index m, a smoke rising slope l, a smoke increment y, a smoke concentration a, and a smoke curvature k. And the sample table thereof can be shown in the following table form.

TABLE 1

Sample Table of Method 1

| Fire Category | Particle Size d | Refractive Index m | Smoke Rising slope l | Smoke Increment y | Smoke Concentration a | Smoke Curvature K |
|---|---|---|---|---|---|---|
| 1 | D1 | M1 | L1 | Y1 | A1 | K1 |
| 2 | D2 | M2 | L2 | Y2 | A2 | K2 |
| 3 | D3 | M3 | L3 | Y3 | A3 | K3 |
| 4 | D4 | M4 | L4 | Y4 | A4 | K4 |
| 5 | D5 | M5 | L5 | Y5 | A5 | K5 |
| 6 | D6 | M6 | L6 | Y6 | A6 | K6 |
| 7 | D7 | M7 | L7 | Y7 | A7 | K7 |
| 8 | D8 | M8 | L8 | Y8 | A8 | K8 |

Each value item can be a value or a value range, for example, D1 may be 0.01 um or 0.01-0.1 um.

In principle, the values or value ranges of various sample parameters of any fire category in the sample table only need to meet the above requirements. Specific values or value ranges of various parameters can be obtained manually or by computer iterative calculation on the basis of collecting an appropriate amount of sample data. Theoretically, more sample data will make the sample table finally obtained more precise, and at the same time, the amount of calculation will also be correspondingly increased. Therefore, the types and numbers of the samples can be selected correspondingly according to the requirements of early-warning precision or use scenarios. It should be noted that the quantity of the samples not only refers to the quantity of combustibles selected for testing, but also includes repeated experimental data for the same combustible under the same or different conditions.

The fire sample may include at least one or all of the following: smoldering fire of 10 pieces of wood, smoldering fire of 90 cotton ropes, open fire of polyurethane plastics, open fire of n-heptane, open fire of 70 pieces of thin wood, open fire of decalin, open fire of newspaper, smoldering fire of 18 pieces of thin wood, open fire of foam, smoldering fire of foam, clothes, shoes, composite boards, books, packing boxes, and plush toys. The interference source sample can include at least one of the following: water vapor, salt fog, kitchen fume, powder, dust, mote, hair, spider silk and small insects. In fact, by incorporating the sample types required by the regulations into the fire sample, the products can directly meet the requirements of the regulations. At the same time, the inclusion of conventional interference sources can greatly reduce the probability of false alarming.

The fire sample and the interference source sample used in the method of the present invention can be set as follows:

The fire sample may include: smoldering fire of 10 pieces of wood, smoldering fire of 90 cotton ropes, open fire of polyurethane plastics, open fire of n-heptane, open fire of 70 pieces of thin wood, open fire of decalin, open fire of newspaper, smoldering fire of 18 pieces of thin wood, open fire of foam, smoldering fire of foam, and other fire samples stipulated in the regulations such as CCCF, EN, and UL for data collection, so that the product of the alarming method meets the relevant requirements of the regulations. And fire data samples are created in a limit state. In addition to this, fire experiments can also be conducted on common materials in daily life to acquire fire data (that is, sample materials include common materials), for example, clothes, shoes, synthetic boards, books, packing boxes, plush toys and so on.

For the collection of interference source data, data of interference sources such as water vapor, salt fog, kitchen fume, powder, dust, mote (suspended particles), hair, spider silk and small insects can be collected, and interference source samples can be created in a limited state.

Step 4: a fire early-warning step of collecting detection data in real time according to the method of step 1, processing the detection data according to the method of step 2 to obtain sample parameters of a to-be-detected sample, and comparing the sample parameters with the sample table obtained in step 3.

If the parameters are in line with the parameters of a fire category, it is determined as a fire and an early-warning signal is sent. If the parameters are not in line with the parameters of any fire category, the above processes are repeated at least twice to calculate mean values, and the mean values are used for comparison. If the mean values are in line with the parameters of a fire category, it is determined as a fire and an early-warning signal is sent. If the mean values are still not in line with the parameters of any fire category, the collection is performed continuously and mean value calculation and comparison are constantly repeated until it is determined as a fire and an early-warning signal is sent after the mean values are in line with the parameters of a fire category; otherwise, the monitoring is continued. Meanwhile, single comparison and determination are also made on data for each detection in multiple detection processes.

The method can be implemented in two parts in practice.

In the first part, the sample table is obtained according to steps 1-3, and stored for backup. The sample table can be stored in the cloud and read through a data link (a 4G network, WIFI and other existing mature communication technologies), and can be fixedly stored in a storage media of the alarm, or stored on a removable media such as a USB flash drive. These three storage manners have their own advantages and disadvantages (the cloud is convenient for optimization and upgrading, but a communication module needs to be added thereto, fixed storage has lower costs but is not conducive to upgrading, and the removable media will also have hardware costs), and can be selected according to requirements. Of course, the actual storage manner is not limited to this, which can also be other methods that can implement the method of the present invention.

In the second part, in the detection and alarming process after the installation is completed, when the method is enabled, detection data is collected in real time according to the method of step 1, then the detection data is calculated and processed according to the method of step 2 to obtain parameters of a detection sample, finally the obtained parameters of the detection sample are compared with the sample table stored in the first part, and judgment is made according to an established comparison method. If the judgment result is that the parameters are in line with the sample table, an early-warning signal is output, and if the parameters are not in line with the sample table, monitoring and judgment are continued.

Another new alarming method for photoelectric smoke detector is wholly the same as the above method, and the difference only lies in that in the method, step 2 is changed appropriately to make the sample parameters include at least one of the following: light intensity ratio n, particle distribution e, smoke rising slope l, smoke increment y, smoke concentration a, and smoke curvature k (that is, the original step 2 is replaced with a new step 2).

The light intensity ratio n and the particle distribution e can be calculated according to the following steps:

the light intensity ratio n satisfies:

$n = I_S1/I_S2$;

where IS1 denotes the scattered light intensity of the scattering angle θ1, and IS2 denotes the scattered light intensity of the scattering angle θ2; and the particle distribution e satisfies:

$e = D(d,m)$; 或, $e = D(n)$;

where d denotes a particle size of a particle, m denotes the refractive index, and n denotes the light intensity ratio; the calculation method is the same as above.

The sample format used by the method (hereinafter referred to as Method 2) is: light intensity ratio n, particle distribution e, smoke rising slope l, smoke increment y, smoke concentration a, and smoke curvature k. And the sample table formed in step 3 may be the following table form:

TABLE 2

Sample Table of Method 2

| Fire Category | Light Intensity Ratio n | Particle Distribution e | Smoke Rising Slope l | Smoke Increment y | Smoke Concentration a | Smoke Curvature K |
|---|---|---|---|---|---|---|
| 1 | N1 | E1 | L1 | Y1 | A1 | K1 |
| 2 | N2 | E2 | L2 | Y2 | A2 | K2 |
| 3 | N3 | E3 | L3 | Y3 | A3 | K3 |
| 4 | N4 | E4 | L4 | Y4 | A4 | K4 |
| 5 | N5 | E5 | L5 | Y5 | A5 | K5 |
| 6 | N6 | E6 | L6 | Y6 | A6 | K6 |
| 7 | N7 | E7 | L7 | Y7 | A7 | K7 |
| 8 | N8 | E8 | L8 | Y8 | A8 | K8 |

Similarly, each value item in the above table can also be a value or a value range.

The smoke rising rate l, the smoke increment y, the smoke concentration a, and the smoke curvature k in the above related step are calculated according to the following methods.

First, a data curve of scattered light intensities of fire smoke particles is drawn by taking time as a horizontal axis and light intensity values as a vertical axis, as shown in FIGS. 2a and 2b.

Then, the smoke rising slope l, the smoke increment y, the smoke concentration a, and the smoke curvature k are calculated according to the drawn data curve of the scattered light intensities of the fire smoke particles. In the curve, a slope from a point A to a point B of the light intensity curve is taken as the smoke rising slope l, an increment from the point A to the point B of the light intensity curve is taken as the smoke increment y, the value of a point a on the light intensity curve is taken as the smoke concentration a, and a change rate between a point k1 and a point k2 of the light intensity curve is taken as the smoke curvature.

The above are two exemplary practical methods, of which one is a method composed of the steps 1, 2, 3 and 4, and the other is a method composed of the step 1, the new step 2, and the steps 3 and 4. The difference between the two methods is that the sample parameters used in step 2 are different, the former includes a particle size d, a refractive index m, a smoke rising rate l, a smoke increment y, a smoke concentration a, and a smoke curvature k, while the latter includes a light intensity ratio n, particle distribution e, a smoke rising rate l, a smoke increment y, a smoke concentration a, and a smoke curvature k. Moreover, their amounts of computation are also different. The two alarming methods are different in that the calculation manners are different and thus the requirements on hardware are different. Upon comparison, the latter has lower requirements on hardware. This is mainly because the calculation process is iterative calculation. For example, in Method 1, values of d and m are set first, α and β are calculated, Ir+Iι is calculated according to the formula 4, the formula 3, the formula 2 and the formula 1 in sequence, and the scattered light intensity IS is obtained finally and compared with the collected scattered light intensity IS. Such an iterative calculation process is repeated until d and m are obtained. Therefore, the latter method can save some amount of computation, which has lower requirements on hardware and is more efficient.

In addition, there are similarities and differences between the contents of the sample parameters in the above two methods and the two are distinguished by Method 1 and Method 2, but it does not mean that the sample parameters in the method of the present invention can only be these or can only be combined in this manner. In fact, the sample parameters on which the method of the present invention is based can be further evolved and combined on the basis of the above two methods, which does not affect the implementation of the method of the present invention.

The sample table can be compared using an exact numerical correspondence method or a weight assignment method. The former means that when various sample parameters of a to-be-compared sample (i.e., a detection sample) are completely consistent with various sample parameters of a certain fire category in the sample table (or within its range, mainly when the sample parameters are range values), it is determined that the sample parameters are in line with the fire category. The weight assignment method refers to assigning the overall weight of each sample parameter in the sample table. During comparison, a fit degree between a detection sample and any fire category is reflected in the form of a ratio. When the ratio exceeds a set threshold, it is determined that the detection sample falls into the fire category. If a sample falls into multiple fire categories simultaneously, the highest ratio shall be used for judging the fire category finally.

For example, for the sample table in Method 1, weights of 40%, 30%, 5%, 3%, 20% and 2% are respectively assigned to the particle size d, the refractive index m, the smoke rising slope l, the smoke increment y, the smoke concentration a, and the smoke curvature k. After comparing the corresponding sample parameters of a detection sample and the sample table, it is found that the sample parameters are in line with the particle size d, the refractive index m, the smoke rising slope l, and the smoke concentration a of the fire category 3, but not in line with the other two items, then the fit degree between the detection sample and the fire category is 40%+30%+5%+20%=95%, and the set threshold is 85%. Thus, it is determined that the detection sample is in line with the fire of the fire category 3.

For the weight assignment method, a specific weight value and a fit threshold of each parameter can be set according to requirements. For example, parameters such as the particle size d, the refractive index m, the smoke concentration a (for Method 1), the light intensity ratio n, the particle distribution e, and the smoke concentration a (for Method 2) are the most important and their weights should not be less than 70% in principle.

Preferably, in step 1, the scattered light intensity data of each sample includes at least a scattered light intensity of a scattering angle θ1, a scattered light intensity of a scattering angle θ2 and scattered light intensity data of a scattering angle θ12, namely scattered signals generated by two emitting apparatuses at different positions and angles. Optimally, the scattered light intensity data is acquired after dynamically modulated optical signals are scattered, and pulse timing sequences, pulse widths and pulse current values of the optical signals at the scattering angle θ1 and the scattering angle θ2 are adjustable.

It is claimed:
1. A detection system for fire detector, comprising a signal modulation module, a photoelectric conversion module and a signal amplification module, the light receiving module is installed at the input end of the photoelectric conversion module and the light emitting module is on the signal modulation module, the output end of the photoelectric conversion module is connected with the input end of the signal amplification module and the output end of the signal amplification module is connected with the input end of the signal modulation module, the signal modulation module deals with the output modulation signal to modulate the emitting mode of the light emitting module.

2. The detection system for fire detector according to claim 1, comprising a signal modulation module that converts the received digital signal into analog modulation signal used for modulating the light emitting mode, wherein the signal modulation module comprises a VCC power supply terminal 1, a resistor R1, a capacitor C1, a resistor R2, a triode Q1, a triode Q2, a resistor R3, a resistor R4, and a level change frequency control terminal P, the light emitting module has its positive electrode connected with the other end of resistor R1-, and its negative electrode connected with the collector of triode Q1; capacitor C1 and capacitor C2 are both connected on the connecting line where the other end of resistor R1 is joined to the positive electrode of the light emitting module; the collector of triode Q2 is joined to the base of resistor R2 and triode Q1 respectively, the emitter of triode Q1 is joined to one end of resistor R3, resistor R4, and its base is joined to one end of resistor R2, the emitter of the triode Q2 is joined to the other end of the resistor R4 before grounded, a plurality of current control branches are joined to the connecting line where the other end of resistor R3 is connected with the base of triode Q2, the other end of the resistor R2 is joined to the level change frequency control terminal P-; or alternatively, a signal modulation module that converts the received digital signal into analog modulation signal used for modulating the emitting mode, wherein the signal modulation module comprises a VCC power supply terminal 2, a resistor R1', a capacitor C1', a resistor R2', a resistor R8, a resistor R9, a triode Q1', a triode Q2', a triode Q3, a triode Q4, a resistor R3', a resistor R4' and a level change frequency control terminal P', VCC supply terminal 2 is connected with one end of resistor R1'; capacitor C1' and Capacitor C2' are both joined to the connecting line where the light emitting module has its positive electrode connected with the other end of resistor R1', and its negative electrode connected with one end of the resistor R8 and the emitter of triode Q3; the base of triode Q3 is joined to the other end of resistor R8 and the collector of the triode Q1' respectively, and its collector is joined to one end of the resistor R4', one end of resistor R3' and the emitter of triode Q1 respectively; the base of triode Q1' is joined to one end of resistor R9, the emitter of triode Q4 and the resistor R2' respectively; the base of triode Q4 is joined to the other end of resistor R9 and the collector of triode Q2' respectively, and its collector, the emitter of triode Q2' is joined to the other end of resistor R4 before grounded, a plurality of current control branches are joined to the connecting line where the base of triode Q2' is joined to the other end of resistor R3', the other end of resistor R2' is joined to the level change frequency control terminal P'; or alternatively,
a signal modulation module that converts the received digital signal into analog modulation signal used for modulating the light emitting mode, wherein the signal modulation module comprises a VCC power supply terminal 3, a resistor R1", a resistor R2", a resistor R3", a resistor R4", a resistor R5, a capacitor C1", a capacitor C3, a triode Q1", a triode Q2", a triode Q3", a field effect transistor Q4, a diode D1, a diode D2 and a level change frequency control terminal P''', the VCC power supply terminal 3 is joined to one end of the resistor R1", the light emitting module has its positive electrode connected with the other end of the resistor R1", capacitor C1" and capacitor C2" are joined to the connecting line between the other end of resistor R1" and the positive electrode of the light emitting module, the light emitting module has its negative electrode joined to the drain of the field effect transistor Q4, the grid of the field effect transistor Q4 is joined to one end of capacitor C3, one end of resistor R3 and the collector of triode Q2" respectively, its source is joined to one end of resistor R4"; the emitter of triode Q2" is joined to the emitter of triode Q1" and the level change frequency control terminal P''' respectively, its base is joined to the base and collector of triode Q1" respectively; the collector of triode Q1" is also joined to the collector of the triode Q3"; the base of the triode Q3" is joined to one end of resistor R2" and the positive electrode of diode D1, a plurality of current control branches are joined to the connecting line where its emitter is connected with one end of resistor R5; diode D1 and diode D2 are both connected in series, the negative electrode of diode D2 is joined to the other end of resistor R5, the other end of resistor R3", the other end of capacitor C3 and the ground terminal respectively, and resistor R4" is also joined to a ground terminal; and the other end of t resistor R2" is joined to the level change frequency control terminal P'''; or alternatively a signal modulation module that converts the received digital signal into analog modulation signal used for modulating the light emitting mode, wherein the signal modulation module comprises a VCC power supply terminal 4, a digital analog conversion module DAC, a capacitor C4, a resistor R6, a resistor R7, a resistor R8 and a Darlington transistor; resistor R6 has one end connected with the VCC supply terminal 4 and the other end connected with the positive electrode of the light emitting module, capacitor C4 and capacitor C5 are both connected on the connecting line where the other end of resistor R6 is connected with the positive electrode of the light emitting module, the negative electrode of the light emitting module is connected with the collector of Darlington transistor; the base of Darlington transistor is joined to one end of resistor R7 and the digital analog conversion module DAC respectively, its emitter is connected with one end of resistor R8; and the other end of resistor R7 and the other end of resistor R8 are joined to each other before grounded; or alternatively, a signal modulation module that converts the received digital signal into analog modulation signal used for modulating the light emitting mode, wherein the signal modulation module comprises a VCC power supply terminal, a digital analog conversion module DAC', a capacitor C4', a resistor R6', a resistor R7', a resistor R8' and a field effect transistor Q5; resistor R6' has one end joined to the VCC supply terminal 4, and has the other end joined to the positive electrode of the light emitting module, capacitor C4' and capacitor C5' connected on the connecting line where the other end of resistor R6' is connected with the positive electrode of the light emitting module, the negative electrode of the light emitting module is joined to the drain of the field effect transistor; the grid of the field effect transistor is joined to one end of the resistor R7 and the digital analog conversion module DAC' respectively, its source is joined to one end of resistor R8'; the other end of resistor R7' and the other end of resistor R8' are joined to each other before grounded.

3. The detection system for fire detector according to claim 1, wherein a voltage dividing circuit and/or a signal distortion preventing module is further provided, the voltage dividing module is joined to the photoelectric conversion module and the signal amplification module respectively, the input end of the voltage dividing module has voltage input; and the output end of the photoelectric conversion module is joined to the input end of the signal amplification module via the signal distortion preventing module.

4. The detection system for the fire detector according to claim 3, wherein the photoelectric conversion module comprises an operational amplifier OP1, a resistor R15, and a capacitor C15; in which, input terminal I1− and input terminal I1+ of the operational amplifier OP1 are respectively joined to both ends of the light receiving module; both ends of resistor R15 are respectively connected to the input terminal I1− and the output terminal O1 of the operational amplifier OP1, and capacitor C15 and resistor R15 are connected in parallel.

5. The detection system for the fire detector according to claim 3, wherein the signal amplification module comprises an operational amplifier OP2, a resistor R17 and a capacitor C16; in which, both ends of resistor R17 are joined to the input terminal I2− and the output terminal O2 of the operational amplifier OP2, capacitor C16 is and resistor R17 are connected in parallel, the input terminal I2+ of the operational amplifier OP2 is lapped to the voltage dividing module, and the output terminal O1 of the operational amplifier OP1 is joined to the output terminal O2 and the input terminal I2− of the operational amplifier OP2 respectively via the signal distortion preventing module.

6. The detection system for the fire detector according to claim 1, further comprising a detection component for a photoelectric smoke detection fire alarm comprising a bottom plate (400), wherein:
the bottom plate(400) is provided with a first emitting tube(401), a second emitting tube(402) and a receiving tube(403), the first emitting tube(401) and the second emitting tube(402) are fitted on the receiving tube(403) in a scattered way, the central axis of the first emitting tube (401) is not overlapping with that of the second emitting tube(402);
the detection component further comprises a scattering mechanism that functions in a way that the optical signals emitted from the first emitting tube (401) and the second emitting tube (402) will not be received directly by the receiving tube (403);
the scattering mechanism comprises an angle control mechanism which is a light-shielding tube and/or a refraction lens disposed at the front end of the first emitting tube (401) and the second emitting tube (402); or
the scattering mechanism comprises screens (404) disposed on the bottom plate (400) and at some point between the first emitting tube (401) and/or the second emitting tube and the receiving tube (403).

7. The detection system for the fire detector according to claim 6, wherein the first emitting tube (401), the second emitting tube (402) and the receiving tube (403) are horizontally disposed on the bottom plate (400) on their respective central axes.

8. The detection system for the fire detector according to claim 6, wherein the first emitting tube (401), the second emitting tube (402) and the receiving tube (403) are obliquely disposed on the bottom plate (400) on their respective central axes.

9. The detection system for the fire detector according to claim 7, wherein the bottom plate(400) is provided with two screens (404), one is disposed on a side of the front part of the first emitting tube(401) in such a way that the optical axis on the side of the first emitting tube(401) is shielded and the optical signals emitted from the first emitting tube(401) will not be directly received by the receiving tube(403), the other (404) is disposed on a side of the head part of the second emitting tube (402) in such a way that the optical axis on the side of the second emitting tube(402) is shielded and the optical signals emitted from the second emitting tube(402) will not be directly received by the receiving tube(403).

10. The detection system for the fire detector according to claim 7, wherein the bottom plate(400) is provided with screens (404), the screens(404) comprise a first shielding part (4041) and a second shielding part (4042), the first shielding part (4041) shields a part of the emitting angles of the first emitting tube (401) such that its optical signals will not be directly received by the receiving tube (403), and the first shielding part (4041) and the second shielding part (4042) cooperatively shield a part of the emitting angles of the second emitting tube (402) such that its optical signals will not be directly received by the receiving tube (403).

11. The detection system for the fire detector according to claim 8, wherein
the bottom plate(400) is further provided with screens (404) which are in the shape of long strip and disposed in the common area among the first emitting tube(401), the second emitting tube(402) and the receiving tube (403), and the screens are provided obliquely and transversely along the horizontal direction in such a way that the optical signals emitted from the first emitting tube(401) and the second emitting tube(402) are not directly received by the receiving tube(403), but instead pass over the top of the screens (404) and contribute to the scattering in all spatial directions.

12. The detection system for the fire detector according to claim 6, wherein the angle θ1 between the central axis of the first emitting tube (401) and that of the receiving tube (403) is 10-55°, and/or alternatively, the angle θ2 between the central axis of the second emitting tube (402) and that of the receiving tube (403) is 70-140°.

13. The detection system for the fire detector according to claim 6, further comprising a photoelectric smoke detection fire alarm including a detector and an optical maze with a base 100, and one side of the base is provided with a maze portion and is fitted with a detector to form a complete alarm, wherein,
the detector has a detection component which is any of the detection components for the photoelectric smoke detection fire alarm;
the maze portion has a maze passage(300) formed by the fitting of a first blocking part (301) and a second blocking part (302), the first blocking part (301) includes a first ridge (311) and a second ridge (312), the second blocking part (302) includes a third ridge (313) and a fourth ridge (314), the included angle between the third ridge (313) and the fourth ridge (314) is an acute angle, and the fourth ridge(314) extends to the region located between the first ridge (311) and the second ridge(312).

14. The detection system for the fire detector according to claim 13, wherein the fourth ridge (314) extends to the joint between the first ridge (311) and the second ridge (312) forming a "Z" shaped maze passage, and more preferably, the end of the fourth ridge is arranged parallel to the second ridge to form a parallel portion.

15. The detection system for the fire detector according to claim 13, wherein the cross sections of the first ridge (311), second ridge (312), third ridge (313) and fourth ridge (314) are straight lines, arcs or curves, and more preferably, the overall cross section of the maze portion is loop, polygon or oval.

16. The detection system for the fire detector according to claim 13, wherein the detector further comprises an upper cover (2) whose interior part is hollow to form a detection cavity (501), at least one part of the detection component is accommodated in the detection cavity (501), the upper cover (2) has a first opening (502) and a second opening (503), and the second opening (503) is fitted with the bottom plate (400) while the first opening (502) is fitted with the optical maze to allow external smoke to enter the detection cavity (501) through the optical maze, then become detected by the detection component.

17. The detection system for the fire detector according to claim 13, wherein the optical maze also has a chamber (101) that is accessible to the detection component and is disposed at the central position of the maze portion, and more preferably, the interior part of the chamber (101) is provided with a guide member (102) comprising a plurality of guide vanes (1021).

18. The detection system for the fire detector according to claim 13, wherein the maze passage (300) is formed by two adjacent maze blocks (200) that are arranged at intervals, the maze block (200) includes a head ridge(210), a middle ridge (220) and a tail ridge (230); the head ridge (210) and the tail ridge (230) are disposed on both ends of the middle ridge (220) respectively in two different directions, the included angle between the middle ridge (220) and the tail ridge (230) is an acute angle, and each maze block (200) is disposed on the base (100) in the same direction;
the tail ridge (230) of the former maze block (200) extends to the region between the head ridge (210) and the middle ridge (220) of the latter maze block (200), the middle ridge (220) and the tail ridge (230) of the former maze block (200) form a third ridge (313) and a fourth ridge (314) of the second blocking part (302) respectively, and the head ridge (210) and the middle ridge (220) of the latter maze block (200) form a first ridge (311) and a second ridge (312) of the first blocking part (301) respectively;
and more preferably, the overall cross section of the maze portion is loop and the cross section of the head ridge is arc.

* * * * *